(12) United States Patent
Fletcher et al.

(10) Patent No.: US 9,090,545 B2
(45) Date of Patent: Jul. 28, 2015

(54) ASYMMETRIC SYNTHESIS OF ORGANIC COMPOUNDS

(71) Applicant: Isis Innovation Limited, Oxford, Oxfordshire (GB)

(72) Inventors: Stephen P. Fletcher, Oxford (GB); Rebecca M. Maksymowicz, Oxford (GB); Philippe M. C. Roth, Oxford (GB)

(73) Assignee: ISIS INNOVATION LIMITED, Oxfordshire (GB)

( * ) Notice: Subject to any disclaimer, the term of this patent is extended or adjusted under 35 U.S.C. 154(b) by 0 days.

(21) Appl. No.: 14/351,240

(22) PCT Filed: Oct. 12, 2012

(86) PCT No.: PCT/GB2012/052537
§ 371 (c)(1),
(2) Date: Apr. 11, 2014

(87) PCT Pub. No.: WO2013/054131
PCT Pub. Date: Apr. 18, 2013

(65) Prior Publication Data
US 2014/0303385 A1    Oct. 9, 2014

(30) Foreign Application Priority Data

Oct. 14, 2011  (GB) .................................. 1117809.2
Sep. 18, 2012  (GB) .................................. 1216666.6

(51) Int. Cl.
| | | |
|---|---|---|
| C07C 205/00 | (2006.01) |
| C07C 45/61 | (2006.01) |
| C07B 53/00 | (2006.01) |
| C07C 45/69 | (2006.01) |
| C07C 49/403 | (2006.01) |
| C07C 49/413 | (2006.01) |
| C07C 49/463 | (2006.01) |
| C07D 309/30 | (2006.01) |
| C07F 7/18 | (2006.01) |
| C07J 1/00 | (2006.01) |
| C07J 21/00 | (2006.01) |

(52) U.S. Cl.
CPC ................ *C07C 45/61* (2013.01); *C07B 53/00* (2013.01); *C07C 45/69* (2013.01); *C07C 49/403* (2013.01); *C07C 49/413* (2013.01); *C07C 49/463* (2013.01); *C07D 309/30* (2013.01); *C07F 7/1892* (2013.01); *C07J 1/0011* (2013.01); *C07J 21/003* (2013.01); C07C 2101/08 (2013.01); C07C 2101/14 (2013.01); C07C 2101/16 (2013.01); C07C 2103/40 (2013.01)

(58) Field of Classification Search
CPC ....................................................... C07B 53/00
USPC .......................................................... 568/312
See application file for complete search history.

(56) References Cited

U.S. PATENT DOCUMENTS

| | | |
|---|---|---|
| 4,147,709 A | 4/1979 | Lynch |
| 4,415,501 A | 11/1983 | Grudzinskas et al. |
| 5,072,010 A | 12/1991 | Lipshutz et al. |
| 5,162,586 A | 11/1992 | Villacorta et al. |
| 5,166,382 A | 11/1992 | Howard et al. |
| 5,286,889 A | 2/1994 | Lipshutz et al. |
| 5,405,981 A | 4/1995 | Lipshutz |
| 5,440,062 A | 8/1995 | Villacorta et al. |
| 6,465,664 B1 | 10/2002 | Buchwald et al. |
| 6,787,655 B2 | 9/2004 | Buchwald et al. |
| 2007/0259774 A1 | 11/2007 | Hartwig et al. |
| 2008/0275274 A1 | 11/2008 | Minnaard et al. |
| 2009/0216025 A1 | 8/2009 | Jamison et al. |

FOREIGN PATENT DOCUMENTS

WO    2007027752    3/2007

OTHER PUBLICATIONS

Wipf et al. Chem. Comm. 1996, 26752676.*
Hart et al. Journal of American Chemical Society, 1974, 96(26), 8115-8116.*
Schwartz et al., Hydrozirconation: A New Transition Metal Reagent for Organic Synthesis, Angew. Chem. Int. Ed. Engl., vol. 15 (1976) No. 6, pp. 333-340.
Schwartz et al., Hydrozirconation. Organic Synthesis via Organozirconium Intermediates, Synthesis and Rearrangement of Alkylzirconium(IV) Complexes and Their Reaction with Electrophiles, J. Am. Chem. Soc., 96, 8115-8116, 1974.
Buchwald et al., Schwartz's Reagent, Org. Syn. Coll., vol. 9, p. 162 (1998); vol. 71, p. 77.
Negishi et al., Reaction of Alkenes and Diemes with t-Butylmagnesium Halides and Zirconocene Dihalides. A Convenient Procedure for Hydrozirconation and a Novel t-Butylzirconation of Conjugated Alkenes, Tet. Lett., 1984, 25, 3407.
Buchwald et al., A Modified Procedure for the Preparation of Cp2Zr(H)Cl Schwartz's Reagent), Tet. Lett. 1987, 28, 3895.
Lipshutz et al., A New Method for the In Situ Generation of Cp2Zr(H)Cl (Schwartz' Reagent), Tet. Lett., 1990, 31, 7257.
Negishi et al., A Convenient Procedure for Hydrozirconation of Alkynes with i-BuZrCp2Cl Generated in Situ by Treatment of Cp2ZrCl2 with t-BuMgCl, J. Org. Chem. 1991, 56, 2590.
Negishi et al., Hydrogen Transfer Hydrozirconation of Alkenes with iBuZrCp2Cl Catalyzed by Lewis-Acidic Metal Compounds Containing Al, Zn, Si, Mg, and Pd, Eur. J. Org. Chem. 1999, 969.
Salomon et al., Cationic Olefin Complexes of Copper(I). Structure and Bonding in Group Ib Metal-Olefin Complexes, J. Am. Chem. Soc. 1973, 1889-1897.

(Continued)

*Primary Examiner* — Nizal Chandrakumar
(74) *Attorney, Agent, or Firm* — Hodgson Russ LLP

(57) ABSTRACT

The present invention provides processes for the production of chiral compounds in a stereoisomeric excess. The present processes involve reacting a hydrometallated alkene compound with a compound comprising a conjugated-bond system under conditions such that the compounds undergo an asymmetric 1,4- or 1,6-conjugate addition reaction, generating a chiral compound in a stereoisomeric excess. The reaction is performed in the presence of a metal catalyst, which catalyst preferably comprises a non-racemic chiral ligand.

12 Claims, No Drawings

(56) References Cited

OTHER PUBLICATIONS

Harutyuanyan et alk., Catalytic Asymmetric Conjugate Addition and Allylic Alkylation with Grignard Reagents, Chem. Rev. 2008, 108, 2824.

Wipf et al., Kinetic vs. Thermodynamic Control in Hydrozirconation Reactions, Pure & Appl. Chem., vol. 70 (5), 1998, 1077-1082.

Feringa et al., Copper-catalyzed asymmetric conjugate addition of Grignard reagents to cyclic enones, Proc. Nat. Acad. Sci. USA, 2004, 101, 5384.

Winn et al., Enantioselective copper catalysed 1,4-conjugate addition reactions using chiral N-hetrocyclic carbenes, Organomet. Chem. 2005, 690, 5672.

Mizutani et al., Cu-Catalyzed Asymmetric Conjugate Additions of Alkylzinc Reagents to Acyclic Aliphatic Enones, J. Am. Chem. Soc., 2002, 124, 779.

Alexakis, A., et al., Enantioselective Copper-Catalyzed Conjugate Addition and Allylic Substitution Reactions, Chemical Reviews, Aug. 1, 2008, vol. 108, No. 8, pp. 2796-2823.

Dzhemilev, U., et al., Hydrometallation of Unsaturated Compounds, Modern Reduction Methods, Jan. 1, 2008, pp. 447-489.

Maksymowicz, R.M., et al., Hydrometallation-asymmetric conjugate addition: application to complex molecule synthesis, Chemical Communications, Jan. 1, 2013, 3 pages.

Maksymowicz, R.M., et al., Catalytic asymmetric carbon—carbon bond formation using alkenes as alkylmetal equivalents, Nature Chemistry, Jul. 15, 2012, vol. 4, pp. 649-654.

Wipf, P., et al., Transmetalation Reactions of Alkylzirconocenes: Copper-Catalyzed Conjugate Addition to Enones, Journal of Organic Chemistry, 1991, vol. 56, pp. 6494-6496.

D'Augustin, M., et al., Enantioselective Copper-Catalyzed Conjugate Addition to Trisubstituted Cyclohexenones: Construction of Stereogenic Quarternary Centers, Angewandte Chemie, International Edition, 2005, vol. 44, pp. 1376-1378.

Vuagnouz-D'Augustin, M., et al., Influence of the Double-Bond Geometry of the Michael Acceptor on Copper-Catalyzed Asymmetric Conjugate Addition, European Journal of Organic Chemistry, 2007, vol. 35, pp. 5852-5860.

Zhang, H., et al., Influence of Copper Salts, Solvents, and Ligands on the Structures of Precatalytic Phosphoramidite Copper Complexes for Conjugate Addition Reactions, Chemistry—A European Journal, 2007, vol. 13, pp. 6691-6704.

Wipf, P., et al., Copper(I)-catalysed asymmetric conjugate addition of organozirconocenes to N-acyl oxazolidinones, Chemical Communications, 1996, vol. 23, pp. 2675-2676.

\* cited by examiner

ASYMMETRIC SYNTHESIS OF ORGANIC COMPOUNDS

FIELD OF THE INVENTION

This invention relates to processes for the production of organic compounds. More particularly, the present invention relates to processes for the asymmetric synthesis of chiral compounds.

BACKGROUND TO THE INVENTION

The development of catalytic methods for asymmetric synthesis is one of the foremost achievements in recent chemistry. At present, many broadly useful methods for catalytic asymmetric oxidation and reduction exist; however, far fewer catalytic asymmetric methods for forming carbon-carbon bonds have been devised. This is not only remarkable in view of the importance of carbon-carbon bond formation in synthesis, but also reflects the major difficulties and challenges associated with enantioselective versions of these transformations. The development of asymmetric carbon-carbon bond forming reactions that are new, powerful and practical is of great importance.

Asymmetric conjugate addition reactions with organometallic reagents are one of the most powerful reactions in chemistry. The use of organozincs and Grignard reagents, readily available from alkylhalides, has made asymmetric catalytic carbon-carbon bond formation based on organometallic reagents practical. However, whilst the use of organozincs and Grignard reagents means that obscure reagents are no longer required, these reagents are still far from ideal. Organometallic procedures have been extensively developed, but suffer from a number of significant limitations. For instance, in the synthesis of complex molecules, functional groups may be present which are incompatible with organometallic reagents. Even the use of a protecting group strategy, which blocks incompatible reaction sites, is often ineffective, due to the reactivity of organometallic reagents and the extreme sensitivity of many asymmetric procedures. Moreover, the reactivity of organometallic reagents is associated with serious safety issues. Asymmetric procedures are typically highly sensitive to reaction conditions such that only particular solvents may be used. Asymmetric organometallic addition reactions must be also be performed at cryogenic temperatures (e.g. less than −30° C.) for high levels of selectively to be obtained. This is not usually possible in industry and so represents a serious limitation of these methods. The aforementioned methods are generally too reactive, too expensive and/or of limited availability.

SUMMARY OF THE INVENTION

According to a first aspect of the present invention, there is provided a process for producing a chiral compound in a stereoisomeric excess, the process comprising:
  (i) contacting a first compound comprising an alkene bond with a hydrometallating agent, wherein the first compound and the hydrometallating agent are contacted under conditions such that the first compound is hydrometallated by said hydrometallating agent; and
  (ii) contacting the hydrometallated first compound with a second compound, wherein the second compound comprises a conjugated π-bond system which is capable of undergoing a 1,4-conjugate addition reaction and which has a carbon atom at said 4-position, wherein the hydrometallated first compound and the second compound are contacted under conditions such that they undergo an asymmetric 1,4-conjugate addition reaction in which a carbon atom of said hydrometallated first compound binds to the carbon atom at said 4-position of the second compound, forming a stereoisomeric excess of a compound having a chiral carbon atom at said 4-position, wherein said asymmetric conjugate addition reaction is performed in the presence of a metal catalyst comprising a non-racemic chiral ligand.

In particular, the present invention provides a process for producing a stereoisomeric excess of a chiral compound of the formula (IV) as defined herein.

Also provided is a process for producing a stereoisomeric excess of a chiral compound of the formula (IVa) as defined herein.

In a second aspect, the present invention provides a process for producing a chiral compound in a stereoisomeric excess, the process comprising:
  (i) contacting a first compound comprising an alkene bond with a hydrometallating agent, wherein the first compound and the hydrometallating agent are contacted under conditions such that the first compound is hydrometallated by said hydrometallating agent; and
  (ii) contacting the hydrometallated first compound with a second compound, wherein the second compound comprises a conjugated π-bond system which is capable of undergoing a 1,6-conjugate addition reaction and which has a carbon atom at said 6-position, wherein the hydrometallated first compound and the second compound are contacted under conditions such that they undergo an asymmetric 1,6-conjugate addition reaction in which a carbon atom of said hydrometallated first compound binds to the carbon atom at said 6-position of the second compound, forming a stereoisomeric excess of a compound having a chiral carbon atom at said 6-position, wherein said asymmetric conjugate addition reaction is performed in the presence of a metal catalyst, said metal catalyst optionally comprising a non-racemic chiral ligand.

In particular, the present invention provides a process for producing a stereoisomeric excess of a chiral compound of the formula (VI) as defined herein.

Processes of the present invention offer various advantages compared with conventional asymmetric carbon-carbon bond formation syntheses. In particular, unactivated alkene substrates may be used as nucleophiles in catalytic asymmetric carbon-carbon bond formation. Alkenes are readily available and have a number of favorable properties when compared to other substrates, such as premade organometallics. The use of simple and readily available materials is highly practical and, through exploitation of the starting materials, may allow rapid access to valuable classes of molecules.

DESCRIPTION OF VARIOUS EMBODIMENTS

For the purposes of the present invention, the following terms as used herein shall, unless otherwise indicated, be understood to have the following meanings.

The term "hydrocarbyl" as used herein refers to a group consisting exclusively of hydrogen and carbon atoms, the group having from 1 to 30 carbon atoms. For instance, a hydrocarbyl group may have from 1 to 20 carbon atoms, e.g. from 1 to 12 carbon atoms, e.g. from 1 to 10 carbon atoms. A hydrocarbyl group may be an acyclic group, a cyclic group, or may comprise both an acyclic portion and a cyclic portion.

Examples of hydrocarbyl groups include alkyl, alkenyl, alkynyl, carbocyclyl (e.g. cycloalkyl, cycloalkenyl or aryl) and aralkyl.

The term "alkyl" as used herein refers to a straight or branched chain alkyl moiety having from 1 to 30 carbon atoms. For instance, an alkyl group may have from 1 to 20 carbon atoms, e.g. from 1 to 12 carbon atoms, e.g. from 1 to 10 carbon atoms. In particular, an alkyl group may have 1, 2, 3, 4, 5 or 6 carbon atoms. Examples of alkyl groups include methyl, ethyl, propyl (n-propyl or isopropyl), butyl (n-butyl, sec-butyl or tert-butyl), pentyl, hexyl and the like.

The term "alkenyl" as used herein refers to a straight or branched chain alkyl group having from 2 to 30 carbon atoms and having, in addition, at least one carbon-carbon double bond, of either E or Z stereochemistry where applicable. For instance, an alkenyl group may have from 2 to 20 carbon atoms, e.g. from 2 to 12 carbon atoms, e.g. from 2 to 10 carbon atoms. In particular, an alkenyl group may have 2, 3, 4, 5 or 6 carbon atoms. Examples of alkenyl groups include ethenyl, 2-propenyl, 1-butenyl, 2-butenyl, 3-butenyl, 1-pentenyl, 2-pentenyl, 3-pentenyl, 1-hexenyl, 2-hexenyl, 3-hexenyl and the like.

The term "alkynyl" as used herein refers to a straight or branched chain alkyl group having from 2 to 30 carbon atoms and having, in addition, at least one carbon-carbon triple bond. For instance, an alkynyl group may have from 2 to 20 carbon atoms, e.g. from 2 to 12 carbon atoms, e.g. from 2 to 10 carbon atoms. In particular, an alkynyl group may have 2, 3, 4, 5 or 6 carbon atoms. Examples of alkynyl groups include ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl, 3-hexynyl and the like.

The term "alkoxy" as used herein refers to —O-alkyl, wherein alkyl is as defined above. In some instances, an alkoxy group may have from 1 to 20 carbon atoms, e.g. from 1 to 12 carbon atoms, e.g. from 1 to 10 carbon atoms. In particular, an alkoxy group may have 1, 2, 3, 4, 5 or 6 carbon atoms. Examples of alkoxy groups include methoxy, ethoxy, propoxy, isopropoxy, butoxy, tert-butoxy, pentoxy, hexoxy and the like.

The term "carbocyclyl" as used herein refers to a saturated (e.g. cycloalkyl) or unsaturated (e.g. cycloalkenyl or aryl) carbocyclic ring moiety having from 3 to 30 carbon atoms. For instance, a carbocyclyl group may have from 3 to 20 carbon atoms, e.g. from 3 to 16 carbon atoms, e.g. from 3 to 10 carbon atoms. In particular, a carbocyclyl group may be a 5- or 6-membered ring system, which may be saturated or unsaturated. Examples of carbocyclic groups include cyclopropyl, cyclobutyl, cyclopentyl, cyclohexyl, phenyl, naphthyl, fluorenyl, azulenyl, indenyl, anthryl and the like.

The term "cycloalkyl" as used herein refers to an aliphatic carbocyclic moiety having from 3 to 20 ring carbon atoms. For instance, a cycloalkyl group may have from 3 to 16 carbon atoms, e.g. from 3 to 10 carbon atoms. In particular, a cycloalkyl group may have 3, 4, 5 or 6 ring carbon atoms. A cycloalkyl group may be a monocyclic, polycyclic (e.g. bicyclic) or bridged ring system. Examples of cycloalkyl groups include cyclopropyl, cyclobutyl, cyclopentyl, cyclohexyl, norbornyl and the like.

The term "cycloalkenyl" as used herein refers to an aliphatic carbocyclic moiety having from 5 to 20 ring carbon atoms and having, in addition, at least one carbon-carbon double bond in the ring. For instance, a cycloalkenyl group may have from 5 to 16 carbon atoms, e.g. from 5 to 10 carbon atoms. In particular, a cycloalkenyl group may have 5 or 6 ring carbon atoms. A cycloalkenyl group may be a monocyclic, polycyclic (e.g. bicyclic) or bridged ring system. Examples of cycloalkenyl groups include cyclopentenyl, cyclohexenyl and the like.

The term "aryl" as used herein refers to an aromatic carbocyclic ring system having from 6 to 30 ring carbon atoms. For instance, an aryl group may have from 6 to 16 ring carbon atoms, e.g. from 6 to 10 ring carbon atoms. An aryl group may be a monocyclic aromatic ring system or a polycyclic ring system having two or more rings, at least one of which is aromatic. Examples of aryl groups include phenyl, naphthyl, fluorenyl, azulenyl, indenyl, anthryl and the like.

The term "aralkyl" as used herein refers to an alkyl group substituted with an aryl group, wherein the alkyl and aryl groups are as defined herein. An example of an aralkyl group is benzyl.

The term "heterocyclyl" as used herein refers to a saturated (e.g. heterocycloalkyl) or unsaturated (e.g. heterocycloalkenyl or heteroaryl) heterocyclic ring moiety having from 3 to 30 ring atoms, wherein said ring atoms include at least one ring carbon atom and at least one ring heteroatom selected from nitrogen, oxygen, phosphorus, silicon and sulphur. For instance, a heterocyclyl group may have from 3 to 20 ring atoms, e.g. from 3 to 16 ring atoms, e.g. from 3 to 10 ring atoms. In particular, a heterocyclyl group may have 5 or 6 ring atoms, and may be saturated or unsaturated. Examples of heterocyclic groups include imidazolyl, thienyl, furyl, tetrahydrofuryl, pyranyl, thiopyranyl, thianthrenyl, isobenzofuranyl, chromenyl, pyrrolyl, pyrrolinyl, pyrrolidinyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, indolizinyl, indolyl, cumaryl, indazolyl, triazolyl, tetrazolyl, purinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, phenanthridinyl, acridinyl, perimidinyl, phenanthrolinyl, furazanyl, phenazinyl, phenothiazinyl, phenoxazinyl, chromenyl, isochromanyl, oxiranyl, azirinyl, 1,2-oxathiolanyl, chromanyl and the like.

The term "heterocycloalkyl" as used herein refers to a saturated heterocyclic moiety having from 3 to 10 ring carbon atoms and 1, 2, 3, 4 or 5 ring heteroatoms selected from nitrogen, oxygen, phosphorus and sulphur. The group may be a monocyclic or polycyclic ring system. Examples of heterocycloalkyl groups include azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl, tetrahydropyranyl, and the like.

The term "heterocycloalkenyl" as used herein refers to a saturated heterocyclic moiety having from 3 to 10 ring carbon atoms and 1, 2, 3, 4 or 5 ring heteroatoms selected from nitrogen, oxygen, phosphorus and sulphur, and having, in addition, at least one carbon-carbon double bond in the ring. The group may be a monocyclic or polycyclic ring system. An example of a heterocycloalkenyl group is pyranyl.

The term "heteroaryl" as used herein refers to an aromatic heterocyclic ring system having from 5 to 30 ring atoms, wherein said ring atoms include at least one ring carbon atom and at least one ring heteroatom selected from nitrogen, oxygen and sulphur. The group may be a monocyclic ring system or a polycyclic (e.g. bicyclic) ring system having two or more rings, at least one of which is aromatic. Examples of heteroaryl groups include pyridazinyl, pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, isoquinolinyl, quinazolinyl and the like.

The terms "halogen" and "halo" as used herein refer to F, Cl, Br or I.

The term "optionally substituted" as used herein means unsubstituted or substituted.

The term "substituted" as used herein in connection with a chemical group means that one or more (e.g. 1, 2, 3, 4 or 5) of the hydrogen atoms in that group are replaced independently of each other by a corresponding number of substituents. It will, of course, be understood that the one or more substituents may only be at positions where they are chemically possible, i.e. that any substitution is in accordance with permitted valence of the substituted atom and the substituent, and that the substitution results in a stable compound. The term is contemplated to include all permissible substituents of a chemical group or compound. It will be understood by those skilled in the art that one or more hydrogen atoms on a given substituent can themselves be substituted, if appropriate.

Where two or more moieties are described as being "each independently" selected from a list of moieties, this means that the moieties may be the same or different. The identity of each moiety is therefore independent of the identities of the one or more other moieties. Where multiple substituents are indicated as being attached to a structure, it will be understood that the substituents can be the same or different.

The term "electron withdrawing group" as used herein refers to any atom or group having an electronegativity greater than that of a hydrogen atom, wherein electronegativity is as defined on the Pauling scale. A quantification of the level of electron withdrawing capability is given by the Hammett sigma ($\sigma$) constant. This constant is well known in the art (see e.g. "Advanced Organic Chemistry", J. March, McGraw Hill, New York, 2007). The Hammett sigma constant values are generally positive for electron withdrawing groups.

The term "$\pi$-bond" as used herein refers to a chemical bond formed by the overlap of p orbitals on adjacent atoms, perpendicular to any sigma ($\sigma$) bonds between the same atoms. A $\pi$-bond is generally a double or triple bond. Examples of $\pi$-bonds include C=C, C≡C, C=O, C=N, C≡N, N=O and S=O bonds.

The term "alkene bond" as used herein refers to an aliphatic carbon-carbon double (C=C) bond.

The present invention provides processes for the asymmetric synthesis of chiral compounds. A process of the invention may involve an asymmetric 1,4-conjugate addition reaction or an asymmetric 1,6-conjugate addition reaction.

Processes Involving an Asymmetric 1,4-Conjugate Addition Reaction

In a first aspect, the present invention provides a process for producing a chiral compound in a stereoisomeric excess (e.g. an enantiomeric or diastereomeric excess), the process comprising:
(i) contacting a first compound comprising an alkene bond with a hydrometallating agent, wherein the first compound and the hydrometallating agent are contacted under conditions such that the first compound is hydrometallated by said hydrometallating agent; and
(ii) contacting the hydrometallated first compound with a second compound, wherein the second compound comprises a conjugated $\pi$-bond system which is capable of undergoing a 1,4-conjugate addition reaction and which has a carbon atom at said 4-position, wherein the hydrometallated first compound and the second compound are contacted under conditions such that they undergo an asymmetric 1,4-conjugate addition reaction in which a carbon atom of said hydrometallated first compound binds to the carbon atom at said 4-position of the second compound, forming a stereoisomeric excess of a compound having a chiral carbon atom at said 4-position, wherein said asymmetric conjugate addition reaction is performed in the presence of a metal catalyst comprising a non-racemic chiral ligand.

The first compound comprises at least one alkene bond, i.e. at least one aliphatic carbon-carbon double (C=C) bond. The first compound may be an acyclic compound, a cyclic compound, or may comprise an acyclic portion and a cyclic portion. The compound may consist exclusively of carbon and hydrogen atoms, or may comprise one or more other atoms in addition. In an embodiment, the first compound is a straight or branched alkene compound having from 2 to 30 carbon atoms, e.g. from 2 to 20 carbon atoms, e.g. from 2 to 12 carbon atoms, e.g. from 2 to 10 carbon atoms, e.g. 2, 3, 4, 5 or 6 carbon atoms. The alkene compound may be unsubstituted or substituted with one or more substituents, e.g. with 1, 2, 3, 4 or 5 substituents selected from $R^a$; hydrocarbyl optionally substituted with 1, 2, 3, 4 or 5 $R^a$; and —$(CH_2)_j$-heterocyclyl optionally substituted with 1, 2, 3, 4 or 5 $R^a$; wherein $R^a$ and j are as defined elsewhere herein.

Preferably, the first compound is a terminal alkene. Terminal alkenes are typically produced annually on the megaton scale, and are among the most readily available organic molecules. These inexpensive raw materials are feedstocks for the preparation of many classes of organic compounds. Catalytic intermolecular reactions using these alkenes may have a tremendous value-added component because they convert inexpensive raw materials into highly functionalised compounds. Alternatively, the first compound may be an internal alkene; such compounds are also readily available and commonly used in chemistry.

The first compound is reacted with a hydrometallating agent under conditions such that the first compound is hydrometallated. Hydrometallation of the first compound will typically result in the addition of a metal atom to one carbon atom of the alkene bond and a hydride ligand to the other. In certain instances, the first compound may undergo one or more intramolecular rearrangements (e.g. beta hydride elimination followed by further hydrometallation) in which the alkene bond relocates to a different position within the first compound, prior to or during reaction with the hydrometallating agent. Thus, for instance, the hydrometallation reaction may result in the attachment of the metal at the sterically less hindered position of the alkene chain. In this case, hydrometallation may occur either by regiospecific addition of the agent to a terminal alkene bond or by addition of the agent to an internal alkene bond followed by rearrangement via metal hydride elimination and readdition to place the metal at a less hindered position of the alkene chain (see e.g. Schwartz et al, Angew. Chem. Int. Ed., 1976, 6, 333). All such hydrometallation reactions fall within the scope of the present invention.

Various hydrometallating agents are known in the art. The hydrometallating agent may comprise a metal (which term encompasses metalloids) and at least one hydride group. By way of illustration, the hydrometallating agent may comprise at least one metal selected from zirconium, titanium, hafnium, niobium, tantalum, boron, aluminium, tin, silicon, magnesium, zinc, palladium, iridium, copper, rhodium, ruthenium, platinum, rhenium, nickel and the like. Preferably, the hydrometallating agent comprises a transition metal. More preferably, the hydrometallating agent comprises zirconium. The hydrometallating agent may be in the form of a metal complex comprising a metal (e.g. a transition metal) bound to one or more ligands, at least one of which is a hydride ligand.

In a preferred embodiment, the hydrometallating agent is a zirconium complex, e.g. a zirconium halohydride complex. In an embodiment, the hydrometallating agent is a zirconium complex of the formula $HZrR_2X$, wherein each R is independently an optionally substituted 6π electron donating ligand (e.g. having 5 carbon atoms, e.g. a π-cyclopentadienyl ligand) and X is another ligand, e.g. selected from halogen, triflates, alcohols and nitrogen-containing compounds. In a preferred embodiment, the hydrometallating agent is a zirconium complex of the formula $HZrCp_2X$, wherein each Cp is an optionally substituted π-cyclopentadienyl ligand and X is a ligand selected from halogen, triflates, alcohols and nitrogen-containing compounds. Preferably, X is halogen. Particularly preferred is a zirconium complex of the formula $HZrCp_2Cl$, which is commonly known in the art as the "Schwartz reagent" (see Schwartz et al, J. Am. Chem. Soc., 96, 8115-8116, 1974).

The hydrometallating agent may be prepared according to procedures known in the art (see e.g. Org. Syn., coll. Col. 9, p. 162 (1998), vol. 71, p 77 (1993); Negishi, Tet. Lett. 1984, 25, 3407; Buchwald, Tet. Lett. 1987, 28, 3895; Lipshutz, Tet. Lett., 1990, 31, 7257; Negishi, J. Org. Chem. 1991, 56, 2590; and Negishi, Eur. J. Org. Chem. 1999, 969).

The hydrometallated first compound is reacted with a second compound, the second compound comprising a conjugated π-bond system which is capable of undergoing a 1,4-conjugate addition reaction and which has a carbon atom at the 4-position. The second compound may be any compound capable of acting as a so-called "Michael acceptor", and will typically be an electrophilic alkene compound. Exemplary compounds include α,β-unsaturated carbonyl compounds (e.g. enones, acrylate esters, acrylamides, maleimides, alkyl methacrylates, acrylamides and vinyl ketones), cyanoacrylates, vinyl sulfones, nitro ethylenes, vinyl phosphonates, acrylonitriles, vinyl pyridines and azo compounds. In a preferred embodiment, the second compound is an α,β-unsaturated carbonyl compound, e.g. an enone.

In an embodiment, the second compound is a dienone. In an embodiment, the second compound is a steroid compound. In a particular embodiment, the second compound is a steroid compound comprising a dienone group.

The hydrometallated first compound and the second compound are contacted under conditions such that they undergo an asymmetric 1,4-conjugate addition reaction to form a chiral compound. Thus, a carbon atom of said hydrometallated first compound to which the metal is attached may bind to the carbon atom at said 4-position of the second compound, forming a stereoisomeric excess of a compound having a chiral carbon atom at said 4-position. The conjugate addition reaction is performed in the presence of a metal catalyst and a non-racemic chiral ligand, yielding a stereoisomeric excess (e.g. an enantiomeric or diastereomeric excess) of the chiral compound.

In an embodiment, the asymmetric 1,4-conjugate addition reaction results in the formation of a quaternary centre at the 4-position.

In particular, the present invention provides a process for producing a chiral compound of the formula (IV) in a stereoisomeric excess (e.g. an enantiomeric or diastereomeric excess):

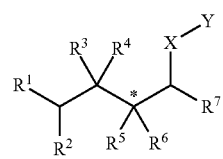

(IV)

wherein $R^1$, $R^2$, $R^3$ and $R^4$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

or $R^1$ and $R^3$ taken together with the carbon atoms to which they are attached may form a carbocyclic or heterocyclic group, which group is optionally substituted with 1, 2, 3, 4 or 5 $R^a$;

$R^5$, $R^6$ and $R^7$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

or $R^5$ and one of $R^7$ and X, taken together with the carbon atoms to which they are attached, may form a carbocyclic or heterocyclic group, which group is optionally substituted with 1, 2, 3, 4 or 5 $R^a$;

X and Y taken together form an electron withdrawing group in which the bond between X and Y is a π-bond;

each $R^a$ is independently selected from halogen, trifluoromethyl, cyano, nitro, oxo, =$NR^b$, —$OR^b$, —$C(O)R^b$, —$C(O)N(R^b)R^c$, —$C(O)OR^b$, —$C(O)SR^b$, —$C(O)SeR^b$, —$OC(O)R^b$, —$S(O)_kR^b$, —$S(O)_kN(R^b)R^c$, —$N(R^b)R^c$, —$N(R^b)N(R^b)R^c$, —$N(R^b)C(O)R^c$ and —$N(R^b)S(O)_kR^b$;

$R^b$ and $R^c$ are each independently hydrogen or selected from hydrocarbyl and —$(CH_2)_j$-heterocyclyl, either of which is optionally substituted with 1, 2, 3, 4 or 5 substituents independently selected from halogen, oxo, cyano, amino, hydroxy, alkyl and alkoxy;

j is 0, 1, 2, 3, 4, 5 or 6;

k is 0, 1 or 2; and the asterisk * designates a chiral centre of (R) or (S) configuration.

The compound of formula (IV) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

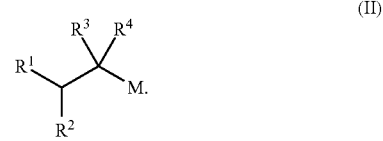

(II)

Thus, for instance, the process may comprise contacting an alkene compound of the formula (I):

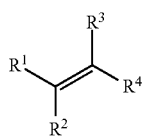

(I)

with a hydrometallating agent of the formula HM under conditions such that the compounds react to form the compound of formula (II).

The compound of the formula (II) is then contacted with a compound of the formula (III):

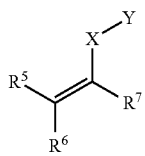

(III)

wherein the compound of formula (II) and the compound of formula (III) are contacted under conditions such that they undergo an asymmetric 1,4-conjugate addition reaction in which a stereoisomeric excess of a compound of formula (IV) is formed. The conjugate addition reaction is performed in the presence of a metal catalyst comprising a non-racemic chiral ligand.

In embodiments, one or more of the following may apply: (i) $R^1$ is hydrocarbyl optionally substituted with 1, 2, 3, 4 or 5 $R^a$; (ii) $R^1$ is alkyl, cycloalkyl or aralkyl, any of which is optionally substituted with 1, 2, 3, 4 or 5 $R^a$; (iii) $R^3$ is hydrogen or hydrocarbyl optionally substituted with 1, 2, 3, 4 or 5 $R^a$; (iv) $R^3$ is hydrogen or alkyl optionally substituted with 1, 2, 3, 4 or 5 $R^a$; (v) $R^1$ and $R^3$ taken together with the carbon atoms to which they are attached form, in the compounds of formulae (II) and (IV), cycloalkyl optionally substituted with 1, 2, 3, 4 or 5 $R^a$; and (vi) $R^2$ and $R^4$ are each hydrogen.

In an embodiment, M comprises a metal selected from zirconium, titanium, hafnium, niobium, tantalum, boron, aluminium, tin, silicon, magnesium, zinc, palladium, iridium, copper, rhodium, ruthenium, platinum, rhenium and nickel. Preferably, M comprises a transition metal.

More preferably, the compound of formula (II) is obtained by hydrozirconation of the compound comprising said alkene bond, e.g. by hydrozirconation of a compound of the formula (I). Thus, in a preferred embodiment, the hydrometallating agent HM comprises zirconium. Preferably, the hydrometallating agent is a zirconium complex of the formula $HZrR_2X$ as defined above. In a preferred embodiment, the hydrometallating agent is a zirconium complex of the formula $HZrCp_2X$ as defined above. Particularly preferred is a zirconium complex of the formula $HZrCp_2Cl$ (the Schwartz reagent).

In embodiments, one or more of the following may apply: (i) $R^5$ is hydrogen or hydrocarbyl optionally substituted with 1, 2, 3, 4 or 5 $R^a$; (ii) $R^5$ is hydrogen or alkyl optionally substituted with 1, 2, 3, 4 or 5 $R^a$; (iii) $R^6$ is hydrogen or hydrocarbyl optionally substituted with 1, 2, 3, 4 or 5 $R^a$; (iv) $R^6$ is hydrogen or alkyl optionally substituted with 1, 2, 3, 4 or 5 $R^a$; and (v) $R^5$ and $R^7$ taken together with the carbon atoms to which they are attached form cycloalkenyl optionally substituted with 1, 2, 3, 4 or 5 $R^a$.

In an embodiment, $R^5$ and $R^6$ are each other than hydrogen such that the chiral centre is a quaternary centre.

In an embodiment:
X and Y taken together form —C(O)$R^8$, —C(O)O$R^8$, —C(O)N$R^8R^9$, —CN, —C(O)S$R^8$, —C(O)Se$R^8$, —SO$_2R^8$, —SO$_2$N$R^8R^9$ or —NO$_2$, wherein $R^8$ and $R^9$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, $C_{1-6}$ alkyl and $C_{1-6}$ alkoxy; or
X is carbon and Y is oxo; and X and $R^5$ taken together with the carbon atoms to which they are attached form a carbocyclic group or a heterocyclic group (e.g. a lactone, thiolactone or lactam), either of which is optionally substituted with 1, 2, 3, 4 or 5 $R^a$.

In an embodiment:
X and Y taken together form —C(O)$R^8$ or —C(O)O$R^8$; or
X is carbon and Y is oxo; and X and $R^5$ taken together with the carbon atoms to which they are attached form a carbocyclic group, which is optionally substituted with 1, 2, 3, 4 or 5 $R^a$.

In an embodiment, the compound of formula (III) is an α,β-unsaturated carbonyl compound.

In an embodiment, the compound of formula (III) is an enone. In a particular embodiment, the compound of formula (III) is a cyclic enone, e.g. a cyclohexenone or a cyclopentenone. In an embodiment, the compound of formula (III) is cyclohex-2-one or cyclopenten-2-one, either of which is optionally substituted with 1, 2, 3, 4 or 5 $R^a$.

In an embodiment, the compound of formula (III) is a dienone. In an embodiment, the compound of formula (III) is a steroid compound. In an embodiment, the compound of formula (III) is a steroid compound comprising a dienone group.

In an embodiment, each $R^a$ is independently selected from acyl, alkoxy, alkoxycarbonyl, alkylamino, alkylsulfinyl, alkylsulfonyl, alkylthio, amino, aminoalkyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy.

The hydrometallated compound undergoes an asymmetric 1,4-conjugate addition reaction with the second compound, forming a chiral compound in a stereoisomeric excess. This reaction occurs in the presence of a metal catalyst comprising a non-racemic chiral ligand. Thus, for instance, the compound of formula (II) and the compound of formula (III) may be reacted in the presence of a metal catalyst comprising a non-racemic chiral ligand, to form a compound of formula (IV) in a stereoisomeric excess. Whilst the first and second compounds will normally be separate compounds, it is envisaged that the processes described herein may also be performed intramolecularly, i.e. using a compound which is capable of being hydrometallated and, moreover, which is capable of undergoing an intramolecular asymmetric 1,4-conjugate addition reaction.

In an embodiment, the metal catalyst comprises a transition metal, e.g. selected from copper, cobalt, iridium, rhodium, ruthenium, nickel, iron, palladium, gold, silver and platinum.

In a preferred embodiment, the metal catalyst comprises copper. In this regard, it has been found that copper can catalyze the conjugate addition of alkylzirconocenes formed in situ from alkenes with high overall yield. The reaction tolerates various functionalities; indeed, functional groups that are not compatible with Grignard reagents and organozincs may be compatible with the processes described herein.

The metal catalyst may comprise any catalytic metal and/or catalyst precursor as it is introduced into the reaction vessel and which may be, if needed, converted in situ into the active form, as well as the active form of the catalyst which participates in the reaction. In embodiments, the metal catalyst is provided in the reaction mixture in an amount of from about 5% to about 10% by weight. The catalyst may be prepared in situ by stirring the metal, non-racemic chiral ligand and any other components (e.g. one or more other ligands) together at e.g. room temperature.

In an embodiment, the metal catalyst is formed from a copper (I) salt comprising a non-coordinating counterion. Preferably, the metal catalyst is formed using a copper triflate salt. Copper triflate benzene complexes have been found to be particularly effective. Copper salts may be prepared in accordance with techniques known in the art. It is also convenient, and effective, to use an air stable copper salt and then exchange the counterion to triflate or another non-coordinating counterion. In particular, copper salts may be prepared by anion exchange with silver salts.

Preferably, the metal catalyst comprises a copper triflate benzene complex. Such complexes may be prepared from copper oxide and triflic anhydride in benzene at reflux. By way of illustration, and without limitation, the following procedure may be used. To a flame dried 250 mL round-bottomed flask under argon, $Cu_2O$ (1 g, 7.00 mmol) and benzene (30 mL) are added. Whilst stirring, triflic anhydride (1.6 mL, 9.5 mmol) is added and the reaction mixture is then heated to reflux until the solution becomes a dark grey, but clear, solution (approximately 4 hours). The reaction mixture is Schlenk filtered into a Schlenk flask under argon. Once filtered, the solution should be clear and the product crashes out almost instantly as a white solid. Once fully cooled, the excess benzene is removed and then the product is washed with dry benzene×3 (all done under argon). The excess benzene is poured off and the solid dried under vacuum. The white powder is stored under argon and when opened has a constant flow of argon flowing over the flask (see Salomon et al, J. Am. Chem. Soc. 1973, 1889-1897).

The metal catalyst comprises at least one non-racemic chiral ligand. The non-racemic chiral ligand may be a chelating ligand or a non-chelating ligand. Examples of suitable ligands include phosphines, bisphosphines, amines, diamines, imines, arsines, sulfides, sulfoxides, carbenes (e.g. N-heterocyclic carbenes), peptides and hybrids thereof, including hybrids of phosphines with amines, hybrids of phosphines with peptides, and hybrids of phosphines with sulfides.

In a preferred embodiment, the non-racemic chiral ligand is a phosphoramidite ligand. Examples of phosphoramidite ligands include the ligands 1, 2, 3 and 4 referred to in the Examples herein. Particularly preferred for use in the present processes is a phosphoramidite ligand of the formula:

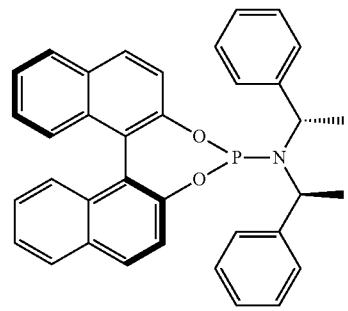

The non-racemic chiral ligand may be used in the form of a purified stereoisomer. The metal catalyst may comprise one or more other ligands, in addition to the at least one non-racemic chiral ligand. In particular, the metal catalyst may include one or more additional ligands as is necessary to obtain a stable complex. The or each ligand can be added to the reaction mixture in the form of a metal complex, or added as a separate reagent relative to the addition of the metal.

The metal catalyst complex may be prepared in accordance with procedures known in the art. By way of illustration, and without limitation, a copper-ligand complex comprising a non-racemic chiral phosphoramidite ligand may be prepared according to the following procedure. A flame dried Schlenk tube, purged with argon, is pre-weighed with a glass stopper. The copper triflate benzene complex is transferred under a blanket of argon to the Schlenk tube and the Schlenk line is placed under vacuum before argon is reintroduced and weighed with the glass stopper in place. One equivalent of phosphoramidite ligand is added to the Schlenk tube while the tube is under a flow of argon and a rubber septa is used to seal. Dry dichloromethane (DCM) is then added via and the mixture is stirred for one hour, before the mixture is cannula filtrated into another dried Schlenk tube, under argon giving a clear solution. The DCM is removed under high vacuum to afford a cream colored solid. The copper-ligand complex is stored under argon.

The various synthetic steps described herein may be performed in separate reaction vessels or in the same reaction vessel (i.e. as a "one-pot" reaction). The process may comprise isolating and/or characterising one or more intermediates, e.g. the hydrometallated alkene, of the process.

Processes according to said first aspect of the present invention will generally be conducted in the presence of one or more solvents. Examples of suitable solvents include dichloromethane, 1,2-dichloroethane, chloroform, $Et_2O$, t-BuOMe, i-$Pr_2O$, 2,2-dimethoxypropane, tetrahydrofuran, 2-methyltetrahydrofuran, diglyme, 1,4-dioxane, toluene, m-xylene and hexane.

In some instances, it may be necessary to include additional reagents in the reaction to promote reactivity of, for example, the transition metal catalyst or other components of the reaction, in order to optimise the yield and/or enantioselectivity of the reaction. In particular, it may be advantageous to include one or more additives such as trimethylsilyl chloride (TMSCl).

In another embodiment, the present invention provides a process for producing a chiral compound of the formula (IVa) in a stereoisomeric excess:

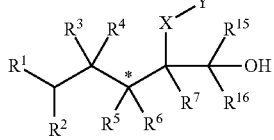

(IVa)

wherein $R^1$, $R^2$, $R^3$, $R^4$, $R^5$, $R^6$, $R^7$, X and Y are as defined above in relation to formula (IV); and $R^{15}$ and $R^{16}$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;

$R^a$ and j are as defined above in relation to formula (IV); and the asterisk * designates a chiral centre of (R) or (S) configuration.

The compound of formula (IVa) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

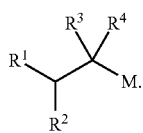

(II)

Thus, for instance, the process may comprise contacting an alkene compound of the formula (I):

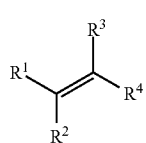

(I)

with a hydrometallating agent of the formula HM under conditions such that the compounds react to form the compound of formula (II).

The compound of the formula (II) is then contacted with a compound of the formula (III):

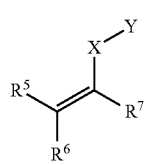

(III)

and a compound of the formula (VII):

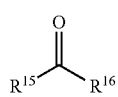

(VII)

wherein the compound of formula (II), the compound of formula (III) and the compound of formula (VII) are contacted under conditions such that they undergo an asymmetric 1,4-conjugate addition reaction to form a stereoisomeric excess of a compound of formula (IVa), wherein said asymmetric conjugate addition reaction is performed in the presence of a metal catalyst comprising a non-racemic chiral ligand.

The compound comprising an alkene bond, the compound of formula (III), the hydrometallating agent, the metal catalyst and the non-racemic chiral ligand may be as defined in any of the embodiments described above in relation to processes for the production of compounds of the formula (IV).

In embodiments, $R^7$ is hydrogen. In embodiments, $R^{15}$ is hydrogen and/or $R^{16}$ is hydrocarbyl optionally substituted with 1, 2, 3, 4 or 5 $R^a$, e.g. alkyl or -alkyl-aryl optionally substituted with 1, 2, 3, 4 or 5 $R^a$.

Processes Involving an Asymmetric 1,6-Conjugate Addition Reaction

In a second aspect, the present invention provides a process for producing a chiral compound in a stereoisomeric excess (e.g. an enantiomeric or diastereomeric excess), the process comprising:

(i) contacting a first compound comprising an alkene bond with a hydrometallating agent, wherein the first compound and the hydrometallating agent are contacted under conditions such that the first compound is hydrometallated by said hydrometallating agent; and (ii) contacting the hydrometallated first compound with a second compound, wherein the second compound comprises a conjugated π-bond system which is capable of undergoing a 1,6-conjugate addition reaction and which has a carbon atom at said 6-position, wherein the hydrometallated first compound and the second compound are contacted under conditions such that they undergo an asymmetric 1,6-conjugate addition reaction in which a carbon atom of said hydrometallated first compound binds to the carbon atom at said 6-position of the second compound, forming a stereoisomeric excess of a compound having a chiral carbon atom at said 6-position, wherein said asymmetric conjugate addition reaction is performed in the presence of a metal catalyst, said metal catalyst optionally comprising a non-racemic chiral ligand.

The first compound comprises at least one alkene bond, i.e. at least one aliphatic carbon-carbon double (C=C) bond. The first compound may be an acyclic compound, a cyclic compound, or may comprise an acyclic portion and a cyclic portion. The compound may consist exclusively of carbon and hydrogen atoms, or may comprise one or more other atoms in addition. In an embodiment, the first compound is a straight or branched alkene compound having from 2 to 30 carbon atoms, e.g. from 2 to 20 carbon atoms, e.g. from 2 to 12 carbon atoms, e.g. from 2 to 10 carbon atoms, e.g. 2, 3, 4, 5 or 6 carbon atoms. The alkene compound may be unsubstituted or substituted with one or more substituents, e.g. with 1, 2, 3, 4 or 5 substituents selected from $R^a$; hydrocarbyl optionally substituted with 1, 2, 3, 4 or 5 $R^a$; and —$(CH_2)_j$-heterocyclyl optionally substituted with 1, 2, 3, 4 or 5 $R^a$; wherein $R^a$ and j are as defined elsewhere herein.

Preferably, the first compound is a terminal alkene. Terminal alkenes are typically produced annually on the megaton scale, and are among the most readily available organic molecules. These inexpensive raw materials are feedstocks for the preparation of many classes of organic compounds. Catalytic intermolecular reactions using these alkenes may have a tremendous value-added component because they convert inexpensive raw materials into highly functionalised compounds. Alternatively, the first compound may be an internal alkene; such compounds are also readily available and commonly used in chemistry.

The first compound is reacted with a hydrometallating agent under conditions such that the first compound is hydrometallated. Hydrometallation of the first compound will typically result in the addition of a metal atom to one carbon atom of the alkene bond and a hydride ligand to the other. In certain instances, the first compound may undergo one or more intramolecular rearrangements (e.g. beta hydride elimination followed by further hydrometallation) in which the alkene bond relocates to a different position within the first compound, prior to or during reaction with the hydrometallating agent. Thus, for instance, the hydrometallation reaction may result in the attachment of the metal at the sterically less hindered position of the alkene chain. In this case, hydrometallation may occur either by regiospecific addition of the agent to a terminal alkene bond or by addition of the agent to an internal alkene bond followed by rearrangement via metal hydride elimination and readdition to place the metal at a less hindered position of the alkene chain (see e.g. Schwartz et al, Angew. Chem. Int. Ed., 1976, 6, 333). All such hydrometallation reactions fall within the scope of the present invention.

Various hydrometallating agents are known in the art. The hydrometallating agent may comprise a metal (which term encompasses metalloids) and at least one hydride group. By way of illustration, the hydrometallating agent may comprise at least one metal selected from zirconium, titanium, hafnium, niobium, tantalum, boron, aluminium, tin, silicon, magnesium, zinc, palladium, iridium, copper, rhodium, ruthenium, platinum, rhenium, nickel and the like. Preferably, the hydrometallating agent comprises a transition metal. More preferably, the hydrometallating agent comprises zirconium. The hydrometallating agent may be in the form of a metal complex comprising a metal (e.g. a transition metal) bound to one or more ligands, at least one of which is a hydride ligand.

In a preferred embodiment, the hydrometallating agent is a zirconium complex, e.g. a zirconium halohydride complex. In an embodiment, the hydrometallating agent is a zirconium complex of the formula $HZrR_2X$, wherein each R is independently an optionally substituted 6π electron donating ligand (e.g. having 5 carbon atoms, e.g. a π-cyclopentadienyl ligand) and X is another ligand, e.g. selected from halogen, triflates, alcohols and nitrogen-containing compounds. In a preferred embodiment, the hydrometallating agent is a zirconium complex of the formula $HZrCp_2X$, wherein each Cp is an optionally substituted π-cyclopentadienyl ligand and X is a ligand selected from halogen, triflates, alcohols and nitrogen-containing compounds. Preferably, X is halogen. Particularly preferred is a zirconium complex of the formula $HZrCp_2Cl$, which is commonly known in the art as the "Schwartz reagent" (see Schwartz et al, J. Am. Chem. Soc., 96, 8115-8116, 1974).

The hydrometallating agent may be prepared according to procedures known in the art (see e.g. Org. Syn., coll. Col. 9, p. 162 (1998), vol. 71, p 77 (1993); Negishi, Tet. Lett. 1984, 25, 3407; Buchwald, Tet. Lett. 1987, 28, 3895; Lipshutz, Tet. Lett., 1990, 31, 7257; Negishi, J. Org. Chem. 1991, 56, 2590; and Negishi, Eur. J. Org. Chem. 1999, 969).

The hydrometallated first compound is reacted with a second compound, the second compound comprising a conjugated π-bond system which is capable of undergoing a 1,6-conjugate addition reaction and which has a carbon atom at the 6-position. The second compound may be any compound capable of acting as a Michael acceptor, and will typically be an electrophilic alkene compound. In a preferred embodiment, the second compound is an unsaturated carbonyl compound comprising at least two alkene bonds that are conjugated with a carbonyl group. In an embodiment, the second compound is a steroid compound.

The hydrometallated first compound and the second compound are contacted under conditions such that they undergo an asymmetric 1,6-conjugate addition reaction to form a chiral compound. Thus, a carbon atom of said hydrometallated first compound to which the metal is attached may bind to the carbon atom at said 6-position of the second compound, forming a stereoisomeric excess of a compound having a chiral carbon atom at said 6-position. The conjugate addition reaction is performed in the presence of a metal catalyst, said catalyst preferably comprising a non-racemic chiral ligand, yielding a stereoisomeric excess (e.g. an enantiomeric or diastereomeric excess) of the chiral compound.

In particular, the present invention provides a process for producing a chiral compound of the formula (VI) in a stereoisomeric excess (e.g. an enantiomeric or diastereomeric excess):

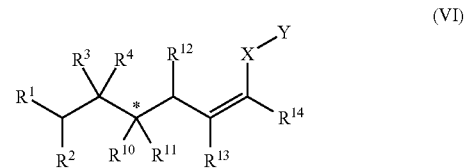

(VI)

wherein
$R^1$, $R^2$, $R^3$ and $R^4$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;
or $R^1$ and $R^3$ taken together with the carbon atoms to which they are attached may form a carbocyclic or heterocyclic group, which group is optionally substituted with 1, 2, 3, 4 or 5 $R^a$;
$R^{10}$, $R^{11}$, $R^{12}$, $R^{13}$ and $R^{14}$ are each independently selected from hydrogen, $R^a$, hydrocarbyl optionally substituted with 1, 2, 3, 4 or 5 $R^a$; and —$(CH_2)_j$-heterocyclyl optionally substituted with 1, 2, 3, 4 or 5 $R^a$;
or two or more (e.g. two or three) of $R^{10}$, $R^{11}$, $R^{12}$, $R^{13}$, $R^{14}$ and X taken together with the carbon atoms to which they are attached, may form a carbocyclic or heterocyclic group, which group is optionally substituted with 1, 2, 3, 4 or 5 $R^a$;
X and Y taken together form an electron withdrawing group in which the bond between X and Y is a π-bond;
each $R^a$ is independently selected from halogen, trifluoromethyl, cyano, nitro, oxo, =$NR^b$, —$OR^b$, —$C(O)R^b$, —$C(O)N(R^b)R^c$, —$C(O)OR^b$, —$C(O)SR^b$, —$C(O)SeR^b$, —$OC(O)R^b$, —$S(O)_kR^b$, —$S(O)_kN(R^b)R^c$, —$N(R^b)R^c$, —$N(R^b)N(R^b)R^c$, —$N(R^b)C(O)R^c$ and —$N(R^b)S(O)_kR^b$;
$R^b$ and $R^c$ are each independently hydrogen or selected from hydrocarbyl and —$(CH_2)_j$-heterocyclyl, either of which is optionally substituted with 1, 2, 3, 4 or 5 substituents independently selected from halogen, oxo, cyano, amino, hydroxy, alkyl and alkoxy;
j is 0, 1, 2, 3, 4, 5 or 6;
k is 0, 1 or 2; and
the asterisk * designates a chiral centre of (R) or (S) configuration.

The compound of formula (VI) may be obtained by first contacting a compound comprising an alkene bond with a hydrometallating agent of the formula HM, wherein M comprises a metal (e.g. a transition metal), wherein said compound and the hydrometallating agent are contacted under conditions such that the compounds react to form a compound of the formula (II):

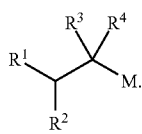
(II)

Thus, for instance, the process may comprise contacting an alkene compound of the formula (I):

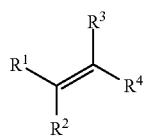
(I)

with a hydrometallating agent of the formula HM under conditions such that the compounds react to form the compound of formula (II).

The compound of the formula (II) is then contacted with a compound of the formula (V):

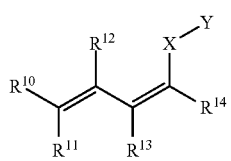
(V)

wherein the compound of formula (II) and the compound of formula (V) are contacted under conditions such that they undergo an asymmetric 1,6-conjugate addition reaction in which a stereoisomeric excess of a compound of formula (VI) is formed. The conjugate addition reaction is performed in the presence of a metal catalyst, said catalyst optionally comprising a non-racemic chiral ligand.

In embodiments, one or more of the following may apply: (i) $R^1$ is hydrocarbyl optionally substituted with 1, 2, 3, 4 or 5 $R^a$; (ii) $R^1$ is alkyl, cycloalkyl or aralkyl, any of which is optionally substituted with 1, 2, 3, 4 or 5 $R^a$; (iii) $R^3$ is hydrogen or hydrocarbyl optionally substituted with 1, 2, 3, 4 or 5 $R^a$; (iv) $R^3$ is hydrogen or alkyl optionally substituted with 1, 2, 3, 4 or 5 $R^a$; (v) $R^1$ and $R^3$ taken together with the carbon atoms to which they are attached form, in the compounds of formulae (II) and (IV), cycloalkyl optionally substituted with 1, 2, 3, 4 or 5 $R^a$; and (vi) $R^2$ and $R^4$ are each hydrogen.

In an embodiment, M comprises a metal selected from zirconium, titanium, hafnium, niobium, tantalum, boron, aluminium, tin, silicon, magnesium, zinc, palladium, iridium, copper, rhodium, ruthenium, platinum, rhenium and nickel. Preferably, M comprises a transition metal.

More preferably, the compound of formula (II) is obtained by hydrozirconation of the compound comprising said alkene bond, e.g. by hydrozirconation of a compound of the formula (I). Thus, in a preferred embodiment, the hydrometallating agent HM comprises zirconium. Preferably, the hydrometallating agent is a zirconium complex of the formula $HZrR_2X$ as defined above. In a preferred embodiment, the hydrometallating agent is a zirconium complex of the formula $HZrCp_2X$ as defined above. Particularly preferred is a zirconium complex of the formula $HZrCp_2Cl$ (the Schwartz reagent).

In embodiments, one or more of the following may apply: (i) $R^{10}$ is hydrogen or hydrocarbyl optionally substituted with 1, 2, 3, 4 or 5 $R^a$; (ii) $R^{10}$ is hydrogen or alkyl optionally substituted with 1, 2, 3, 4 or 5 $R^a$; (iii) $R^{11}$ is hydrogen or hydrocarbyl optionally substituted with 1, 2, 3, 4 or 5 $R^a$; (iv) $R^{11}$ is hydrogen or alkyl optionally substituted with 1, 2, 3, 4 or 5 $R^a$; (v) $R^{12}$ is hydrogen or hydrocarbyl optionally substituted with 1, 2, 3, 4 or 5 $R^a$; (vi) $R^{13}$ is hydrogen or alkyl optionally substituted with 1, 2, 3, 4 or 5 $R^a$; (vii) $R^{14}$ is hydrogen or hydrocarbyl optionally substituted with 1, 2, 3, 4 or 5 $R^a$; and (viii) $R^{14}$ is hydrogen or alkyl optionally substituted with 1, 2, 3, 4 or 5 $R^a$.

In an embodiment, X and Y taken together form $—C(O)R^8$, $—C(O)OR^8$, $—C(O)NR^8R^9$, $—CN$, $—C(O)SR^8$, $—C(O)SeR^8$, $—SO_2R^8$, $—SO_2NR^8R^9$ or $—NO_2$, wherein $R^8$ and $R^9$ are each independently hydrogen or selected from hydrocarbyl and $—(CH_2)_j$-heterocyclyl, either of which is optionally substituted with 1, 2, 3, 4 or 5 substituents independently selected from halogen, oxo, cyano, amino, hydroxy, $C_{1-6}$ alkyl and $C_{1-6}$ alkoxy.

In an embodiment, X and Y taken together form $—C(O)R^8$ or $—C(O)OR^8$.

In an embodiment, X is carbon and Y is oxo; and X and one or more (e.g. one or two) of $R^{10}$, $R^{11}$, $R^{12}$, $R^{13}$ and $R^{14}$ taken together with the carbon atoms to which they are attached form a carbocyclic or heterocyclic group, either of which is optionally substituted with 1, 2, 3, 4 or 5 $R^a$. In an embodiment, said carbocyclic or heterocyclic group is a multicyclic group, e.g. comprising 2, 3, 4 or 5 rings. In an embodiment, the compound of formula (V) is a steroid compound.

In an embodiment, each $R^a$ is independently selected from acyl, alkoxy, alkoxycarbonyl, alkylamino, alkylsulfinyl, alkylsulfonyl, alkylthio, amino, aminoalkyl, aralkyl, cyano, dialkylamino, halo, haloalkoxy, haloalkyl, hydroxy, formyl, nitro, alkyl (optionally substituted with e.g. alkoxy, hydroxy, haloalkoxy, halogen or haloalkyl), aryl (optionally substituted with e.g. alkoxy, hydroxy, haloalkoxy, halogen, alkyl or haloalkyl), heteroaryl (optionally substituted with e.g. alkoxy, hydroxy, haloalkoxy, halogen, alkyl or haloalkyl), heterocycloalkyl (optionally substituted with e.g. alkoxy, hydroxy, haloalkoxy, halogen, alkyl or haloalkyl), aminoacyl, aminosulfonyl, acylamino, sulfonylamino, heteroarylalkyl, aryloxy, heteroaryloxy, arylalkyloxy and heteroarylalkyloxy.

The hydrometallated compound undergoes an asymmetric 1,6-conjugate addition reaction with a second compound, forming a chiral compound in a stereoisomeric excess. This reaction occurs in the presence of a metal catalyst, said metal catalyst preferably comprising a non-racemic chiral ligand. Thus, for instance, the compound of formula (II) and the compound of formula (V) may be reacted in the presence of a metal catalyst, said metal catalyst preferably comprising a non-racemic chiral ligand, to form a compound of formula (VI) in a stereoisomeric excess. Whilst the first and second compounds will normally be separate compounds, it is envisaged that the processes described herein may also be performed intramolecularly, i.e. using a compound which is capable of being hydrometallated and, moreover, which is capable of undergoing an intramolecular asymmetric 1,6-conjugate addition reaction.

In an embodiment, the metal catalyst comprises a transition metal, e.g. selected from copper, cobalt, iridium, rhodium, ruthenium, nickel, iron, palladium, gold, silver and platinum.

In a preferred embodiment, the metal catalyst comprises copper. In this regard, it has been found that copper can catalyze the conjugate addition of alkylzirconocenes formed in situ from alkenes with high overall yield. The reaction tolerates various functionalities; indeed, functional groups that are not compatible with Grignard reagents and organozincs may be compatible with the processes described herein.

The metal catalyst may comprise any catalytic metal and/or catalyst precursor as it is introduced into the reaction vessel and which may be, if needed, converted in situ into the active form, as well as the active form of the catalyst which participates in the reaction. In embodiments, the metal catalyst is provided in the reaction mixture in an amount of from about 5% to about 10% by weight. The catalyst may be prepared in situ by stirring the metal, non-racemic chiral ligand and any other components (e.g. one or more other ligands) together at e.g. room temperature.

In an embodiment, the metal catalyst is formed from a copper (I) salt comprising a non-coordinating counterion. Preferably, the metal catalyst is formed using a copper triflate salt. Copper triflate benzene complexes have been found to be particularly effective. Copper salts may be prepared in accordance with techniques known in the art. It is also convenient, and effective, to use an air stable copper salt and then exchange the counterion to triflate or another non-coordinating counterion. In particular, copper salts may be prepared by anion exchange with silver salts.

Preferably, the metal catalyst comprises a copper triflate benzene complex. Such complexes may be prepared from copper oxide and triflic anhydride in benzene at reflux. By way of illustration, and without limitation, the following procedure may be used. To a flame dried 250 mL round-bottomed flask under argon, $Cu_2O$ (1 g, 7.00 mmol) and benzene (30 mL) are added. Whilst stirring, triflic anhydride (1.6 mL, 9.5 mmol) is added and the reaction mixture is then heated to reflux until the solution becomes a dark grey, but clear, solution (approximately 4 hours). The reaction mixture is Schlenk filtered into a Schlenk flask under argon. Once filtered, the solution should be clear and the product crashes out almost instantly as a white solid. Once fully cooled, the excess benzene is removed and then the product is washed with dry benzene×3 (all done under argon). The excess benzene is poured off and the solid dried under vacuum. The white powder is stored under argon and when opened has a constant flow of argon flowing over the flask (see Salomon et al, J. Am. Chem. Soc. 1973, 1889-1897).

In an embodiment, the second compound (e.g. the compound of formula (V) is a chiral compound which is substantially stereochemically pure. In this case, a non-racemic chiral ligand may not be required in order to obtain a stereoisomeric excess of the product compound.

Preferably, the metal catalyst comprises at least one non-racemic chiral ligand. The non-racemic chiral ligand may be a chelating ligand or a non-chelating ligand. Examples of suitable ligands include phosphines, bisphosphines, amines, diamines, imines, arsines, sulfides, sulfoxides, carbenes (e.g. N-heterocyclic carbenes), peptides and hybrids thereof, including hybrids of phosphines with amines, hybrids of phosphines with peptides, and hybrids of phosphines with sulfides.

In a preferred embodiment, the non-racemic chiral ligand is a phosphoramidite ligand. Examples of phosphoramidite ligands include the ligands 1, 2, 3 and 4 referred to in the Examples herein. Particularly preferred for use in the present processes is a phosphoramidite ligand of the formula:

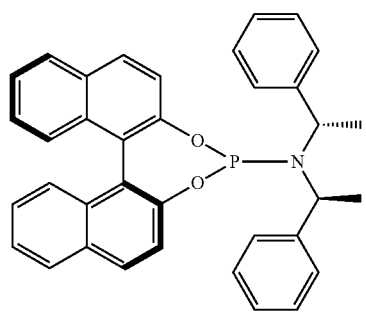

The non-racemic chiral ligand may be used in the form of a purified stereoisomer. The metal catalyst may comprise one or more other ligands, in addition to the at least one non-racemic chiral ligand. In particular, the metal catalyst may include one or more additional ligands as is necessary to obtain a stable complex. The or each ligand can be added to the reaction mixture in the form of a metal complex, or added as a separate reagent relative to the addition of the metal.

The metal catalyst complex may be prepared in accordance with procedures known in the art. By way of illustration, and without limitation, a copper-ligand complex comprising a non-racemic chiral phosphoramidite ligand may be prepared according to the following procedure. A flame dried Schlenk tube, purged with argon, is pre-weighed with a glass stopper. The copper triflate benzene complex is transferred under a blanket of argon to the Schlenk tube and the Schlenk line is placed under vacuum before argon is reintroduced and weighed with the glass stopper in place. One equivalent of phosphoramidite ligand is added to the Schlenk tube while the tube is under a flow of argon and a rubber septa is used to seal. Dry dichloromethane (DCM) is then added via and the mixture is stirred for one hour, before the mixture is cannula filtrated into another dried Schlenk tube, under argon giving a clear solution. The DCM is removed under high vacuum to afford a cream colored solid. The copper-ligand complex is stored under argon.

The various synthetic steps described herein may be performed in separate reaction vessels or in the same reaction vessel (i.e. as a "one-pot" reaction). The process may comprise isolating and/or characterising one or more intermediates, e.g. the hydrometallated alkene, of the process.

Processes according to said second aspect of the present invention will generally be conducted in the presence of one or more solvents. Examples of suitable solvents include dichloromethane, 1,2-dichloroethane, chloroform, $Et_2O$, t-BuOMe, i-$Pr_2O$, 2,2-dimethoxypropane, tetrahydrofuran, 2-methyltetrahydrofuran, diglyme, 1,4-dioxane, toluene, m-xylene and hexane.

In some instances, it may be necessary to include additional reagents in the reaction to promote reactivity of, for example, the transition metal catalyst or other components of the reaction, in order to optimise the yield and/or enantioselectivity of the reaction. In particular, it may be advantageous to include one or more additives such as trimethylsilyl chloride (TMSCl).

By way of illustration, a process of the present invention may be conducted in accordance with one of the procedures described in the Examples or elsewhere herein. It will be understood that the processes described in the Examples are solely for the purpose of illustrating the invention and should not be construed as limiting. A process utilising similar or analogous reagents and/or conditions known to one skilled in the art may also be used to obtain a compound of the invention. Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

The present processes produce a chiral compound (e.g. the compound of formula (IV), the compound of formula (IVa) or the compound of formula (VI)) in a stereoisomeric excess, i.e. such that the concentration of one stereoisomer of the chiral compound exceeds the concentration of another stereoisomer. That is, the present processes yield a chiral compound with a stereoisomeric excess of greater than zero. Preferably, the present processes yield a product with a stereoisomeric excess of greater than 20%, greater than 50%, greater than 70%, greater than 80%, or greater than 90%. The chiral compound may be enantiomeric or diastereomeric. For instance, the desired compound may be obtained in a substantially pure form (e.g. a form having a purity of greater than 80% purity, in particular greater than 90%, 95% or 99%) of a single enantiomer or diastereomer. In an embodiment, the chiral compound is enantiomeric. All stereoisomers are included within the scope of the present invention. Where a single enantiomer or diastereoisomer is disclosed, the present invention also extends to the other enantiomers or diastereoisomers.

Stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the stereoisomers by conventional means (e.g. HPLC, chromatography over silica).

Compounds of the present invention may also exhibit geometrical isomerism. The present invention contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

Compounds of the present invention (especially those containing heteroatoms and conjugated bonds) may also exist in tautomeric forms, and all such tautomers are included in the scope of the present invention. In particular, the present compounds (e.g. the compounds of the formula (IV), the compounds of formula (IVa) or the compounds of formula (VI)) may be obtained and isolated in the form of enolates and other tautomeric forms; once again, all such tautomeric forms are included within the scope of the present invention. The present invention also extends to all other variant forms of the defined compounds, for example salts, esters, acids or other variants of the present compounds and their tautomers.

Advantageously, a process of the present invention may be efficient, selective, direct, and may occur at easily accessible temperatures. By avoiding extra steps and protecting groups these methods are environmentally friendly compared to currently available technology. The present invention also introduces the highly practical concept of using inexpensive, functional group tolerant alkenes in a number of useful transformations to synthetic chemists.

The present processes are particularly relevant to industry. A process of the invention may further comprise formulating a product comprising the chiral compound or converting the chiral compound into a product. In an embodiment, the product is a pharmaceutical product, a cosmetic product, a fragrance, a foodstuff, a petrochemical product or a polymer product.

In particular, the present processes may be utilised in the production of active pharmaceutical ingredients, e.g. prostaglandins. Thus, the chiral compound may be formulated together with one or more pharmaceutically acceptable carriers or excipients, to provide a pharmaceutical formulation; or chemically converted to a pharmaceutically active ingredient. Moreover, where the chiral compound is an active pharmaceutical ingredient, the compound may be obtained in the form of a free acid or base, or in the form of a pharmaceutically acceptable salt thereof. The term "pharmaceutically acceptable salt" refers to acid addition salts or base addition salts of the compounds in the present invention. Pharmaceutically acceptable salts include salts of both inorganic and organic acids.

The following non-limiting Examples illustrate the present invention.

EXAMPLES

General Procedures

Examples 1 to 5

In Examples 1 to 5, an alkene hydrozirconation reaction was first performed using the Schwartz reagent ($Cp_2ZrHCl$). The hydrozirconated alkene was then reacted with a cyclic enone according to one of the following general procedures.

General Procedure 1

In a flame dried round-bottomed flask under argon, the copper (I) salt (10 mol %) and ligand (10 mol %) were added. $CH_2Cl_2$ (1 mL) was added and the solution was allowed to stir for 1 h. The hydrozirconated alkene was added dropwise to the mixture and stirred for 5 min before the addition of the α,β-unsaturated ketone. The reaction mixture was arbitrarily allowed to stir at room temperature overnight. The reaction was quenched with wet $Et_2O$ and 1 M $NH_4Cl$, the aqueous layer was extracted with $Et_2O×3$ then the combined organic layers washed with sat. $NaHCO_3$. The resulting solution was dried with $Na_2SO_4$, filtered and the solvent removed in vacuo.

General Procedure 2

In a flame dried round-bottomed flask under argon, copper (I) salt (10 mol %) and ligand (10 mol %) were added. $CH_2Cl_2$ (1 mL) was added and the solution was allowed to stir for 1 h. The flask was covered in tin foil before the addition of the silver salt (14 mol %) and the reaction mixture stirred for an additional hour before the hydrozirconated alkene was added dropwise to the mixture. After 5 min the α,β-unsaturated ketone was added and the reaction mixture arbitrarily allowed to stir at room temperature overnight. The reaction was quenched with wet Et$_2$O and 1 M NH$_4$Cl, the aqueous layer was extracted with Et$_2$O×3 then the combined organic layers washed with sat. NaHCO$_3$. The resulting solution was dried with Na$_2$SO$_4$, filtered and the solvent removed in vacuo.

General Procedure 3

The hydrozirconated alkene was added dropwise to a stirred solution of a premade catalyst complex (e.g. complex 4 below) (30 mg, 0.04 mmol, 0.1 eq) in Et$_2$O (2 mL), and allowed to stir for 10 minutes. The unsaturated ketone (0.4 mmol, 1 eq) was added and the resulting mixture stirred until consumption of the starting material as indicated by TLC. The reaction was quenched with wet Et$_2$O and 1 M NH$_4$Cl, the aqueous layer was extracted with Et$_2$O×3 then the combined organic layers washed with sat. NaHCO$_3$. The resulting solution was dried with Na$_2$SO$_4$, filtered and the solvent removed in vacuo.

With regard to the catalyst complex, copper (I) complexes comprising one of the phosphoramidite ligands 1, 2, and 3 were found to be particularly effective. The copper triflate ligand complex 4 was found to be especially effective. Use of copper salts prepared by anion exchange with silver salts is also highly effective.

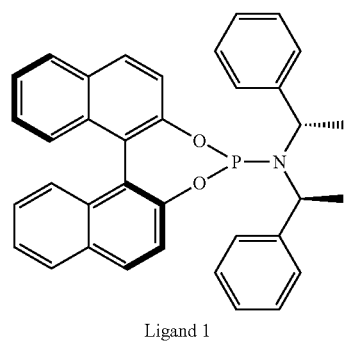

Ligand 1

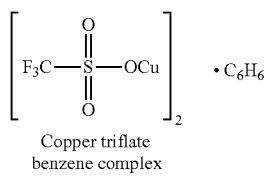

Copper triflate
benzene complex

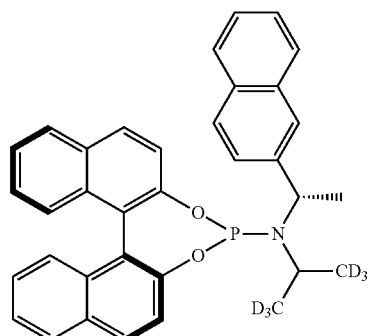

Ligand 2

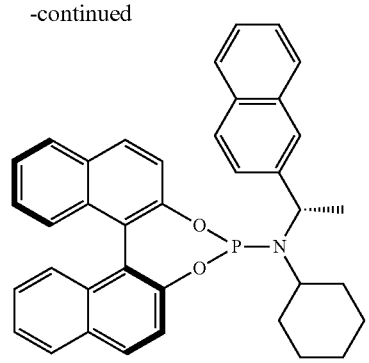

Ligand 3

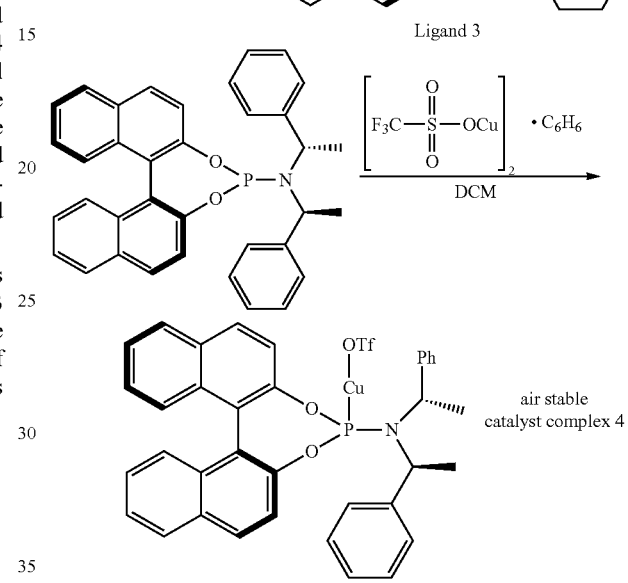

air stable
catalyst complex 4

The catalyst complexes could be prepared in situ by stirring the various components together at room temperature. It is also convenient, and effective, to use an air stable copper salt and then exchange the counterion to triflate or another non-coordinating counterion.

Example 1

Synthesis of 3-hexylcyclohexanone

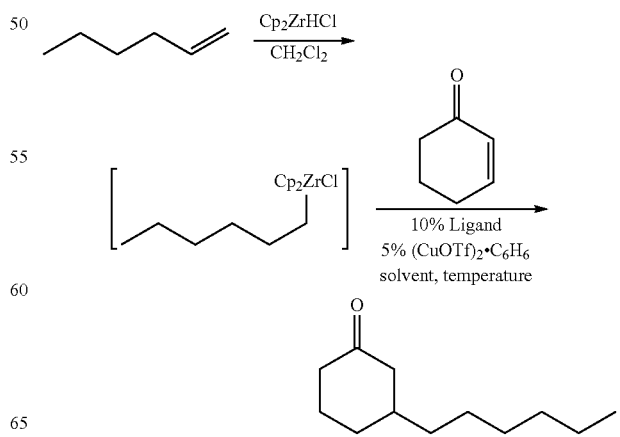

1-hexene (0.06 mL, 0.5 mmol) and CH$_2$Cl$_2$ (0.5 mL) were added to a flame dried 5 mL round-bottomed flask under argon with stirring. Bis(cyclopentadienyl)zirconium chloride hydride (Schwartz reagent, 103 mg, 0.4 mmol) was added and the reaction mixture was allowed to stir at room temperature until the reaction becomes a homogeneous yellow solution. The above-mentioned general procedures were then used to perform the conjugate addition reaction. The product compound was characterised using $^1$H NMR and $^{13}$C NMR. The presence of an enantioexcess was determined by derivatization and comparison of the $^{13}$C NMR spectrum to that of the racemic material that had been derivatised in the same way. Specifically, the crude 1,4-conjugate addition reaction mixture was transferred to a vial with CDCl$_3$. Then, 3 Å mol. sieves and (1R,2R)-(+)-1,2-Diphenylethylenediamine ((R,R)-Dpen, ca. 1.5-2 eq) were added. The vial was shaken and allowed to stand for at least 1 h before being transferred to an NMR tube and submitted for $^{13}$C NMR (500 MHz, 1024 scans).

Example 2

Synthesis of 3-(2-cyclohexylethyl)-4,4-dimethylcyclohexanone

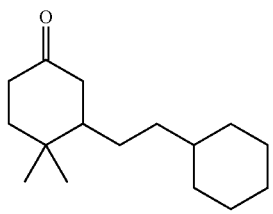 [SMILES: CC1(C)CCC(=O)CC1CCC1CCCCC1]

Using 4,4-dimethylcyclohex-2-enone (53 µL, 0.40 mmol) as substrate and vinylcyclohexene (0.14 mL, 1 mmol, 2.5 eq) as reagent and following General Procedure 3 overnight gave the above product (72 mg, 0.30 mmol, 75%) as a colourless oil after purification by column chromatography (1:49 EtOAc/petrol). The product compound was characterised using $^1$H NMR and $^{13}$C NMR, IR and MS. The presence of an enantioexcess was determined by derivatization using the procedure described in Example 1.

Example 3

Effect of Solvent and Temperature

Using hexene and cyclohexenone as model substrates, a variety of solvents were examined. A range of conditions were found to be effective at room temperature, and results could also be optimized by adjusting temperature (for example entries 10 and 13 in Table 1).

TABLE 1

| Entry | Solvent | Temperature (° C.) | Selectivity (% e.e.) |
|---|---|---|---|
| 1 | CH$_2$Cl$_2$ | RT | 89 |
| 2 | CH$_2$Cl$_2$ | 30 | 84 |
| 3 | CH$_2$Cl$_2$ | reflux | 73 |
| 4 | 1,2-dichloroethane | RT | 75 |
| 5 | chloroform | RT | 80 |
| 6 | Et$_2$O | RT | 85 |
| 7 | t-BuOMe | RT | 84 |
| 8 | i-Pr$_2$O | RT | 84 |
| 9 | 2,2-dimethoxypropane | RT | 86 |
| 10 | THF | 5 | 92 |
| 11 | THF | RT | 80 |
| 12 | 2-Me-THF | 5 | 93 |
| 13 | 2-Me-THF | 10 | 94 |
| 14 | 2-Me-THF | RT | 88 |
| 15 | 2-Me-THF | 40 | 73 |
| 16 | diglyme | RT | 89 |
| 17 | diglyme | 40 | 75 |
| 18 | 1,4-Dioxane | RT | 75 |
| 19 | toluene | RT | 83 |
| 20 | m-xylene | RT | 75 |
| 21 | hexane | RT | 75 |

Example 4

Effect of Additives

Additives can increase the yield and enantioselectivity of the reaction, for example TMSCl effects the reaction by increasing the ee of the product (typically by 5-10%). The work in Table 2 was done with added TMSCl. Examination of a variety of alkenes illustrated that this is a general reaction and good yields and enantioselectivity can be obtained with a wide variety of alkenes, including those with functional groups.

TABLE 2

| Alkene | product | yield | ee |
|---|---|---|---|
| (CH$_2$=CHCH$_2$CH$_2$Ph) | (4,4-dimethyl-3-(4-phenylbutyl)cyclohexanone) | 74 | 89 |

Reaction scheme: 1) alkene, Cp$_2$ZrHCl, CH$_2$Cl$_2$, RT; catalytic ligand complex, ether, RT; 2) Starting material; TMSCl TABLE 2-continued

| Alkene | product | yield | ee |
|---|---|---|---|
| PhCH₂CH₂CH₂CH₂CH=CH₂ | 4,4-dimethyl-3-(5-phenylpentyl)cyclohexanone | 65 | 89 |
| styrene | 4,4-dimethyl-3-(2-phenylethyl)cyclohexanone | 44 | 80 |
| 1-hexene | 4,4-dimethyl-3-pentylcyclohexanone | 67 | 89 |
| 1-octene | 4,4-dimethyl-3-heptylcyclohexanone | 49 | 89 |
| 1-tridecene | 4,4-dimethyl-3-dodecylcyclohexanone | 70 | 89 |
| vinylcyclohexane | 3-(2-cyclohexylethyl)-4,4-dimethylcyclohexanone | 74 | 93 |
| 3,3-dimethyl-1-butene | 4,4-dimethyl-3-(3,3-dimethylbutyl)cyclohexanone | 65 | 87 |

TABLE 2-continued

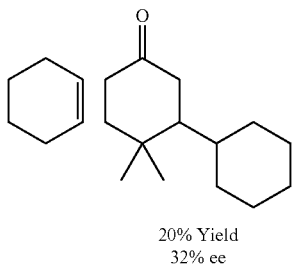

Example 5

Internal Alkenes

The above-mentioned procedures were also used with internal alkenes. Quaternary centres can also be formed with good levels of enantioselectivity. Standard conditions could be applied, without any further optimisation to obtain the results below.

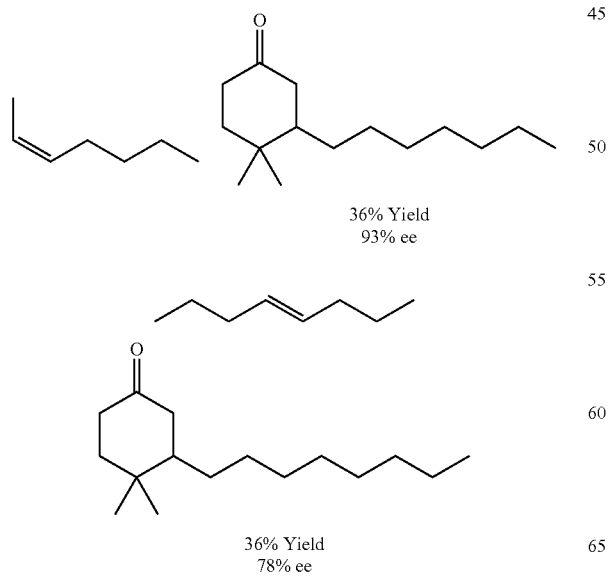

-continued

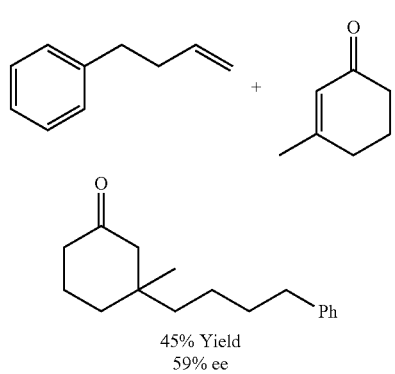

Example 6

The following compounds were synthesised following procedures analogous to those described in Examples 1 to 5:

| Entry | Substrate | Product | Yield[a] | ee[b] |
|---|---|---|---|---|
| 1 (n = 1) | | 3 (n = 1) | 74% | 89%[c,d] |
| 2 (n = 3) | | 4 (n = 3) | 65% | 89%[c] |
| 3 (n = 1) | | 5 (n = 1) | 67% | 89%[d] |
| 4 (n = 9) | | 6 (n = 9) | 70% | 89%[d] |
| 5[e] | | 7 | 65% | 84%[d] |
| 6 (X = CH$_2$) | | 8 (X = CH$_2$) | 74% | 93%[d] |
| 7 (X = CH) | | 9 (X = CH) | 60%[f] | 87%[d] |
| 8[g] | | 10 | 71% | 78%[d] |
| 9 | | 11 | 56% | 82%[c] |

-continued
| | | | | |
|---|---|---|---|---|
| 10 | 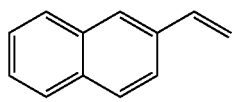 | 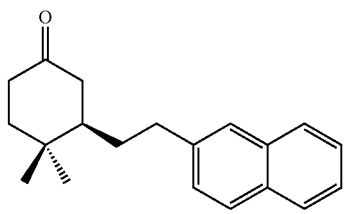
12 | 52% | 71%[c] |
| 11 (n = 1)
12 (n = 2) | 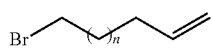 | 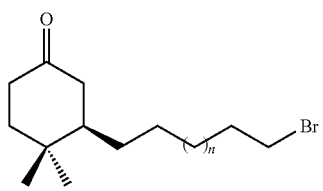
13 (n = 1)
14 (n = 2) | 66%
58% | 76%[c,d]
76%[c,d] |
| 13 | 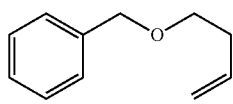 | 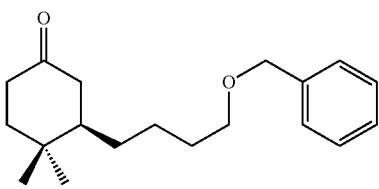
15 | 54% | 80%[c] |
| 14 | 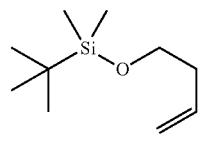 | 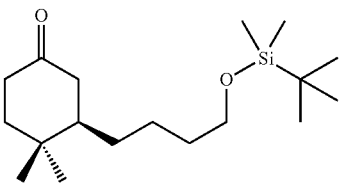
16 | 49% | 94%[d] |
| 15 | 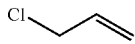 | 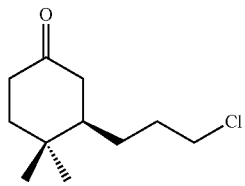
17 | 19% | 71%[d] |
| 16[h] | 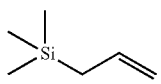 | 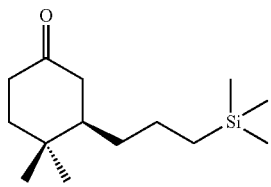
18 | 53% | 96%[d] |

| | | | | |
|---|---|---|---|---|
| 17[e] | 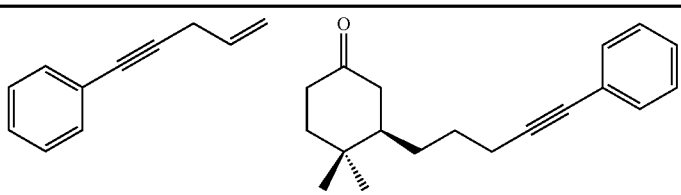 | | 62% | 72%[c] |
| | 19 | | | |
| 18 19 | 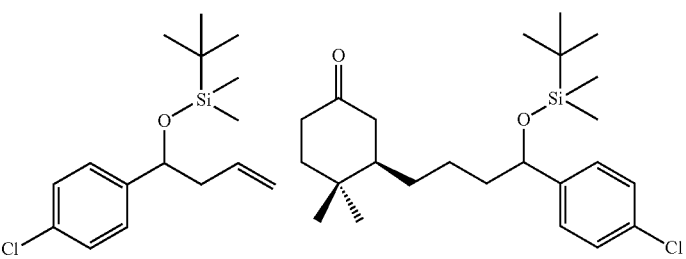 | | 62%[f] | 85%[d, i] |
| | 20 | | | |
| | large scale with 5% cat 93%, 70% ee | | | |
| Entry | Enone | Product | Yield[a] | ee[b] |
|---|---|---|---|---|
| 1a 1b[d] | 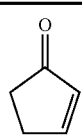 | 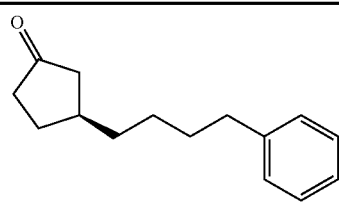 21 | 23% 29% | 75%[c] 85%[c] |
| 2 R = Ph 3 R = CH₂CH₃ | 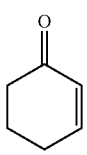 | 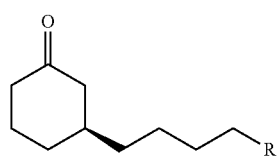 1 (R = Ph) 2 (R = CH₂CH₃) | 59% 59% | 90%[c, e] 93%[e] |
| 4 | 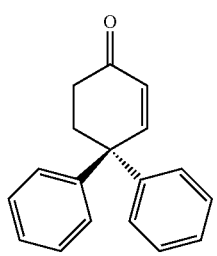 | 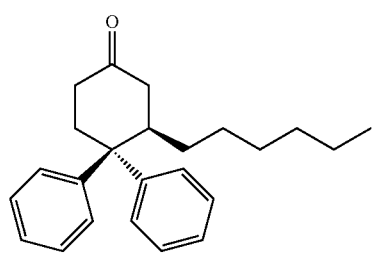 22 | 75% | 90%[c] |
| 5 | 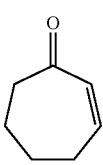 | 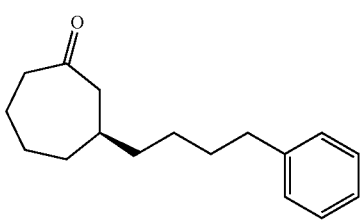 23 | 73% | 91%[c] |

| | | | |
|---|---|---|---|
| 6 | 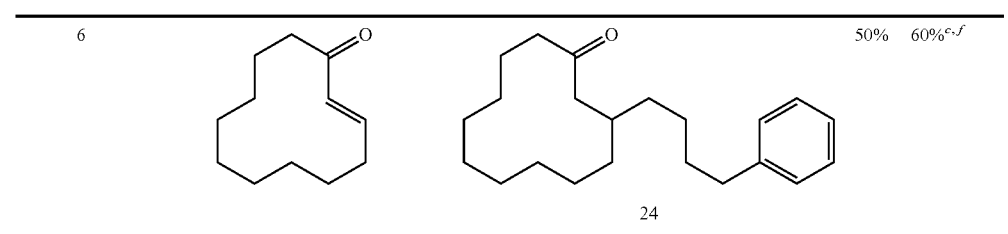 | 50% | 60%[c,f] |
| | 24 | | |

[In the above tables, the indices c-i indicate the use of different techniques by which the configuration of the compounds or the presence of an enantiomeric excess was determined, or minor variations in the process conditions.]

General Procedures

Examples 7 to 15

Methods

Procedures using oxygen- and/or moisture-sensitive materials were performed with anhydrous solvents (vide infra) under an atmosphere of anhydrous argon in flame-dried flasks, using standard Schlenk techniques. Analytical thin-layer chromatography was performed on precoated glass-backed plates (Silica Gel 60 $F_{254}$; Merck), and visualised using a combination of UV light (254 nm) and aqueous ceric ammonium molybdate (CAM), aqueous basic potassium permanganate stains or vanillin solution. Flash column chromatography was carried out using Apollo Scientific silica gel 60 (0.040-0.063 nm), Merck 60 Å silica gel, VWR (40-63 µm) silica gel and Sigma Aldrich silica gel. Pressure was applied at the column head via hand bellows or a flow of nitrogen with the solvent system used in parentheses. Cooling of reaction mixtures to 0° C. was achieved using an ice-water bath. Other temperatures were obtained using a Julabo FT902 immersion cooler.

Unless stated otherwise, solution NMR spectra were recorded at room temperature; $^1H$ and $^{13}C$ nuclear magnetic resonance experiments were carried out using Bruker DPX-200 (200/50 MHz), DPX-400 (400/100 MHz), DQX-400 (400/100 MHz) or AVC-500 (500/125 MHz) spectrometers. Chemical shifts are reported in ppm from the residual solvent peak. Chemical shifts (b) are given in ppm and coupling constants (J) are quoted in hertz (Hz). Resonances are described as s (singlet), d (doublet), t (triplet), q (quartet) and m (multiplet). Labels H and H' refer to diastereotopic protons attached to the same carbon and impart no stereochemical information. Assignments were made with the assistance of gCOSY, DEPT-135, gHSQC and gHMBC or gHMQC NMR spectra. Numbering and names of structures accompanying reported data is non-IUPAC, and solely for reference.

Low-resolution mass spectra were recorded using a Walters LCT premier XE. High-resolution mass spectra (EI and ESI) were recorded using a Bruker MicroTOF spectrometer by the internal service at the University of Oxford.

Chiral HPLC separations were achieved using an Agilent 1230 Infinity series normal phase HPLC unit and HP Chemstation software. Chiralpak® columns (250×4.6 mm), fitted with matching Chiralpak® Guard Cartridges (10×4 mm), were used as specified in the text. Solvents used were of HPLC grade (Fisher Scientific, Sigma Aldrich or Rathburn); all eluent systems were isocratic.

Infrared measurements (neat, thin film) were carried out using a Bruker Tensor 27 FT-IR with internal calibration in the range 4000-600 $cm^{-1}$.

Optical rotations were recorded using a Perkin-Elmer 241 Polarimeter. CD spectra were recorded using an Applied Photophysics ChiraScan CD/Fluorometer.

Materials

Dry THF, $CH_2Cl_2$, $Et_2O$, PhMe, benzene, hexane, pentane, DME, acetonitrile and 1,2-dichloroethane were collected fresh from an mBraun SPS-800 solvent purification system having been passed through anhydrous alumina columns. Dry tert-butyl methyl ether and 2-Me-THF were purchased from Acros with an AcroSeal®. All other dry solvents used were dried over 3 Å molecular sieves and stored under argon. All other solvents were used as purchased from Sigma Aldrich, Rathburn or Fisher Scientific.

Unless stated otherwise, commercially available reagents were purchased from Sigma-Aldrich, Fisher Scientific, Apollo Scientific, Acros Organics, Strem Chemicals, Alfa Aesar or TCI UK and were used without purification. Petroleum ether refers to light petroleum boiling in the range 40-60° C. TMSCl, styrene, allyl chloride and 4,4-dimethyl-cyclohex-2-enone were distilled before use and stored in Schlenk flasks under an argon atmosphere. Deuterated solvents were purchased from Sigma-Aldrich ($CD_2Cl_2$, $CDCl_3$). Schwartz reagent was prepared according to a literature procedure from $Cp_2ZrCl_2$ provided by Alfa Aesar or Strem Chemicals. $(CuOTf)_2 \cdot C_6H_6$ was synthesised using a modified literature procedure[2] and carefully maintained under an inert atmosphere. $(CuOTf)_2 \cdot C_6H_6$ should be a white or off-white powder, not green or brown. 2-vinylnaphthalene was recrystallised from hexane before use.

Preparation of Copper-Ligand Complex:

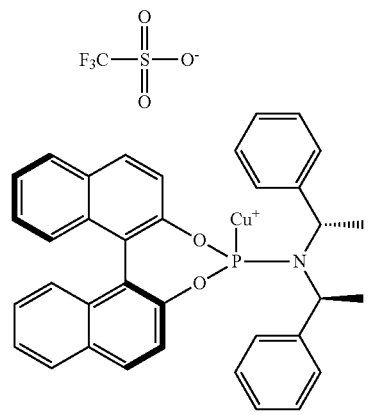

To a flame dried Schlenk flask containing $(CuOTf)_2 \cdot (C_6H_6)$ (239 mg, 0.48 mmol, 0.5 eq.) at room temperature under an argon atmosphere was added the phosphoramidite ligand (513 mg, 0.95 mmol, 1.0 eq.) and then CH$_2$Cl$_2$ (10 mL). This mixture was stirred for 1 h before the resulting clear colourless solution was cannula filtrated into another Schlenk flask. The solvent was then gently removed by use of an oil-pump vacuum (with liquid nitrogen trapping). The resulting off-white solid was dried for at least one extra hour under oil-pump vacuum before storing the catalyst complex under argon.

$^1$H NMR (500 MHz, CD$_2$Cl$_2$) δ$_H$/ppm 1.89 (d, J=6.7 Hz, 6H) 4.59-4.71 (m, 2H) 7.19-7.44 (m, 6H) 7.45-7.61 (m, 10H) 7.69 (d, J=8.8 Hz, 2H) 7.94-8.07 (m, 3H) 8.14 (d, J=8.8 Hz, 1H); $^{13}$C NMR (125 MHz, CD$_2$Cl$_2$) δ$_C$/ppm 22.0 (2C), 53.8 (2C under solvent peak), 121.1, 121.2, 122.1, 123.60, 123.64, 125.90, 125.97, 126.9, 127.1, 127.2, 127.7, 127.8 (4C), 128.5 (2C), 128.7, 129.0, 129.6 (4C), 131.2, 131.5, 132.5, 132.80, 133.0, 141.37, 141.41, 148.2 (d, J=3.9 Hz), 149.4 (d, J=14.2 Hz); $^{31}$P NMR (200 MHz, CD$_2$Cl$_2$) δ$_P$/ppm 124.1 (br, s); $^{19}$F NMR: (500 MHz, CD$_2$Cl$_2$) δ$_F$/ppm −78.2 (s); HRMS (EI): m/z calcd for C$_{36}$H$_{30}$CuNO$_2$P [M-CF$_3$O$_3$S]$^+$: 602.1310. found: 602.1319. Also found: CuL$_2$ calcd for C$_{72}$H$_{60}$CuN$_2$O$_4$P$_2$ [M]$^+$: 1141.3324. found: 1141.3325. IR: (v$_{max}$/cm$^{-1}$): 633, 670, 748, 827, 949, 1025, 1223.

Procedure A: Catalytic Asymmetric Conjugate Addition with Copper-Ligand Complex Formed In Situ:

(CuOTf)$_2$.(C$_6$H$_6$) (10.1 mg, 0.02 mmol, 0.05 eq.) and the phosphoramidite ligand (21.6 mg, 0.04 mmol, 0.1 eq.) were dissolved in Et$_2$O (2.0 mL) under an argon atmosphere and allowed to stir for 1 h at room temperature. In another flask, Cp$_2$ZrHCl (206.0 mg, 0.80 mmol, 2.0 eq.) was added to a stirred, room temperature, solution of alkene (1.0 mmol, 2.5 eq.) in CH$_2$Cl$_2$ (0.40 mL) under an argon atmosphere. After stirring for 40 min, the resulting clear yellow solution was transferred via syringe over about 1 min to the stirred solution containing the copper and ligand under an argon atmosphere. The resulting dark mixture was allowed to stir for an additional 10 min before cyclic enone (0.40 mmol, 1.0 eq.) and then TMSCl (0.26 mL, 2.0 mmol, 5.0 eq.) were added dropwise via syringe. The reaction was stirred until complete (TLC control (EtOAc/Petrol 1:2.5)). The reaction was quenched by the addition of Et$_2$O (ca 3 mL) and then NH$_4$Cl (1 M aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo to give an oil. Flash column chromatography of the residue (EtOAc/petrol; SiO$_2$) gave the desired steroid product.

Procedure B: Catalytic Asymmetric Conjugate Addition with Premade Copper-Ligand Complex:

Cp$_2$ZrHCl (206 mg, 0.80 mmol, 2.0 eq.) was added to a stirred, room temperature, solution of alkene (1.0 mmol, 2.5 eq.) in CH$_2$Cl$_2$ (0.40 mL) under an argon atmosphere. After stirring for about 40 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before cyclic enone (0.40 mmol, 1.0 eq.) and then TMSCl (0.26 mL, 2.0 mmol, 5.0 eq.) were added dropwise via syringe. The reaction was stirred until complete (TLC control (EtOAc/Petrol 1:2.5)). The reaction was quenched by the addition of Et$_2$O (ca 3 mL) and then NH$_4$Cl (1 M. aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo to give an oil. Flash column chromatography of the residue (EtOAc/petrol; SiO$_2$) gave the desired steroid product.

Example 7

(+)-1α-hexyl-4-androstene-3,17-dione (1)

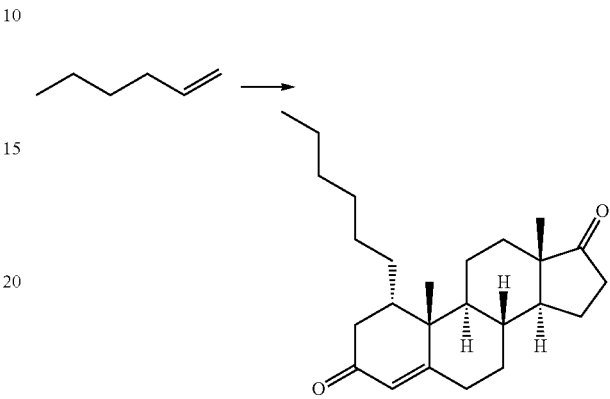

Procedure A: (CuOTf)$_2$.(C$_6$H$_6$) (10.1 mg, 0.02 mmol, 0.05 eq.) and the phosphoramidite ligand (21.6 mg, 0.040 mmol, 0.10 eq.) were dissolved in Et$_2$O (2.0 mL) under an argon atmosphere and allowed to stir for 1 h at room temperature. In another flask, Cp$_2$ZrHCl (206.0 mg, 0.80 mmol, 2.0 eq.) was added to a stirred, room temperature, solution of 1-hexene (0.13 mL, 1.0 mmol, 2.5 eq.) in CH$_2$Cl$_2$ (0.40 mL) under an argon atmosphere. After stirring for 40 min, the resulting clear yellow solution was transferred via syringe over about 1 min to the stirred solution containing the copper and ligand under an argon atmosphere. The resulting dark mixture was allowed to stir for an additional 10 min before 1,4-androstadiene-3,17-dione (114.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et$_2$O (ca 3 mL) and NH$_4$Cl (1 M aq., ca 1.5 mL). The mixture was partitioned between the aqueous and Et$_2$O layers and the former phase was extracted with Et$_2$O (3×10 mL). The combined organic phase was washed with NaHCO$_3$ (sat. aq., ca 10 mL), dried (Na$_2$SO$_4$), filtered and concentrated in vacuo to give an oil. Flash column chromatography of the yellow residue (5:30:65 EtOAc/DCM/petrol; SiO$_2$) gave major diastereomer (1) (+)-1α-hexyl-4-androstene-3,17-dione (75 mg, 0.20 mmol, 50%) and minor diastereomer (1a) (+)-1α-hexyl-4-androstene-3,17-dione (24 mg, 0.064 mmol, 16%). Diastereomeric ratio (3.6:1) was determined by integration of $^1$H NMR spectra.

Major Diastereomer 1: $^1$H NMR (400 MHz, CDCl$_3$) δ$_H$/ppm 0.84 (t, J=6.9 Hz, 3H), 0.91 (s, 3H), 1.00-1.29 (m, 10H), 1.32 (s, 3H), 1.33-1.66 (m, 7H), 1.67-1.80 (m, 1H), 1.80-2.03 (m, 4H), 2.09 (dt, J=19.1, 9.0 Hz, 1H), 2.31-2.39 (m, 1H), 2.39-2.54 (m, 3H), 2.56-2.64 (m, 1H), 5.70 (br. s, 1H); $^{13}$C NMR (100 MHz, CDCl$_3$) δ$_C$/ppm 13.7, 14.1, 19.5, 20.5, 21.7, 22.6, 27.1, 27.4, 29.4, 29.8, 31.2, 31.7, 32.7, 35.0, 35.7, 37.9, 41.7, 41.8, 46.3, 47.5, 51.0, 124.0, 167.8, 199.0, 220.5; HRMS (ESI) m/z calcd for C$_{25}$H$_{38}$NaO$_2$ [M+Na]$^+$: 393.2764. found: 393.2748; [α]$^{20}_{589}$=+140.9 (c 1.12, CHCl$_3$); IR (v$_{max}$/cm$^{-1}$) 1455, 1671, 1738, 2926.

(+)-1α-hexyl-4-androstene-3,17-dione (1a)

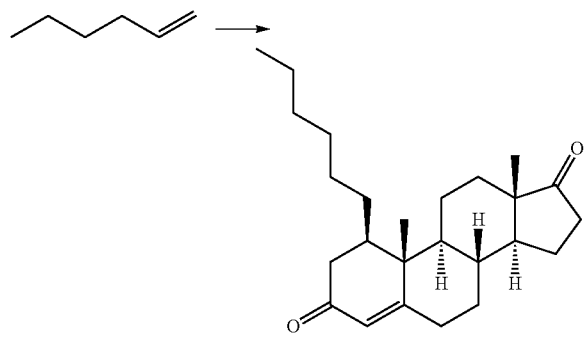

Minor Diastereomer 1a: $^1$H NMR (400 MHz, CDCl3) $\delta_H$/ppm 0.87 (t, J=6.8 Hz, 3H), 0.91 (s, 3H), 1.06-1.15 (m, 2H), 1.16 (s, 3H), 1.19-1.43 (m, 11H), 1.46-1.64 (m, 3H), 1.65-1.77 (m, 1H), 1.81-2.00 (m, 4H), 2.01-2.16 (m, 2H), 2.20-2.31 (m, 2H), 2.40-2.55 (m, 3H), 5.79 (br. s, 1H); $^{13}$C NMR (100 MHz, CDCl3) $\delta_C$/ppm 13.8, 14.1, 16.3, 21.9, 22.3, 22.6, 27.8, 29.5, 30.1, 31.4, 31.7, 33.1, 33.8, 35.5, 35.7, 38.6, 40.1, 43.2, 47.6, 50.9, 53.4, 123.0, 170.7, 199.2, 220.3; HRMS (ESI) m/z calcd for $C_{25}H_{38}NaO_2$ [M+Na]$^+$: 393.2764 found: 393.2753; [α]$^{20}_{589}$=+14.7 (c 1.05, CHCl$_3$); IR ($v_{max}$/cm$^{-1}$): 1454, 1673, 1738, 2926.

Example 8

(+)-7α-hexyl-17α-hydroxy-3-oxo-pregn-4-ene-21-carboxylic acid γ-lactone (2)

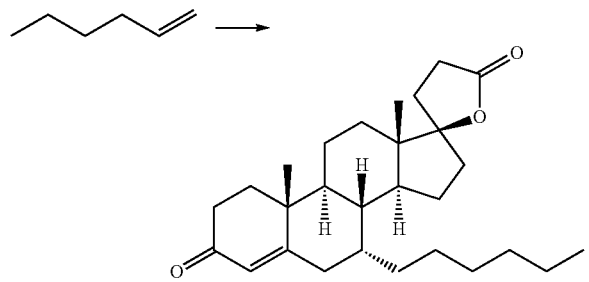

Procedure A: $(CuOTf)_2 \cdot (C_6H_6)$ (10.1 mg, 0.02 mmol, 0.05 eq.) and the phosphoramidite ligand (21.6 mg, 0.040 mmol, 0.10 eq.) were dissolved in Et$_2$O (2.0 mL) under an argon atmosphere and allowed to stir for 1 h at room temperature. In another flask, Cp$_2$ZrHCl (206.0 mg, 0.80 mmol, 2.0 eq.) was added to a stirred, room temperature, solution of 1-hexene (0.13 mL, 1.0 mmol, 2.5 eq.) in CH$_2$Cl$_2$ (0.40 mL) under an argon atmosphere. After stirring for 40 min, the resulting clear yellow solution was transferred via syringe over about 1 min to the stirred solution containing the copper and ligand under an argon atmosphere. The resulting dark mixture was allowed to stir for an additional 10 min before Canrenone (136.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et$_2$O (ca 3 mL) and NH$_4$Cl (1 M aq., ca 1.5 mL). The mixture was partitioned between the aqueous and Et$_2$O layers and the former phase was extracted with Et$_2$O (3×10 mL). The combined organic phase was washed with NaHCO$_3$ (sat. aq., ca 10 mL), dried (Na$_2$SO$_4$), filtered and concentrated in vacuo to give an oil. Flash column chromatography of the yellow residue (30:70 EtOAc/petrol; SiO$_2$) gave major diastereomer (2) (+)-7α-hexyl-17α-hydroxy-3-oxo-pregn-4-ene-21-carboxylic acid γ-lactone (101 mg, 0.24 mmol, 59%) and minor diastereomer (2a) (+)-1α-hexyl-4-androstene-3,17-dione (35 mg, 0.082 mmol, 21%). Diastereomeric ratio (4.8:1) was determined by integration of $^1$H NMR spectra.

Major diastereomer 2: $^1$H NMR (400 MHz, CDCl$_3$) $\delta_H$/ppm 0.88 (t, J=6.7 Hz, 3H), 0.99 (s, 3H), 1.02-1.20 (m, 5H), 1.21 (s, 3H), 1.23-1.51 (m, 11H), 1.51-1.89 (m, 7H), 1.89-1.99 (m, 1H), 2.02-2.10 (m, 1H), 2.21-2.30 (m, 1H), 2.30-2.47 (m, 4H), 2.47-2.62 (m, 2H), 5.73 (br. s, 1H); $^{13}$C NMR (100 MHz, CDCl$_3$) $\delta_C$/ppm 14.1, 14.4, 18.1, 20.7, 22.4, 22.6, 25.2, 27.3, 29.3, 29.5, 31.2, 31.5, 31.9, 34.0, 35.3, 36.0, 36.1, 36.6, 38.6, 39.3, 44.8, 45.6, 46.9, 95.8, 125.9, 169.5, 176.7, 199.1; HRMS (ESI) m/z calcd for $C_{28}H_{42}NaO_3$ [M+Na]$^+$: 449.3026 found: 449.3017; [α]$^{20}_{589}$=+37.3 (c 1.00, CHCl$_3$); IR ($v_{max}$/cm$^{-1}$): 1192, 1669, 1769, 2927.

(+)-7β-hexyl-17α-hydroxy-3-oxo-pregn-4-ene-21-carboxylic acid γ-lactone (2a)

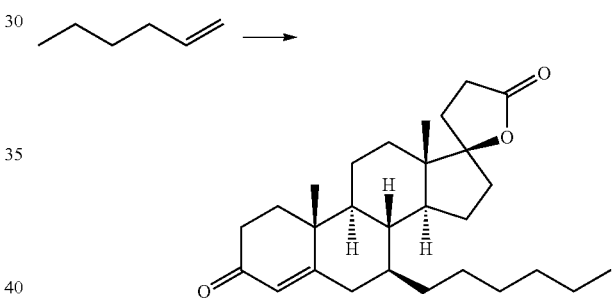

Minor Diastereomer 2a: $^1$H NMR (400 MHz, CDCl$_3$) $\delta_H$/ppm 0.88 (t, J=6.8 Hz, 3H), 0.99 (s, 3H), 1.17 (s, 3H), 1.19-1.52 (m, 15H), 1.52-1.84 (m, 7H), 1.84-1.99 (m, 2H), 1.99-2.09 (m, 1H), 2.16-2.32 (m, 3H), 2.32-2.46 (m, 2H), 2.46-2.63 (m, 2H), 5.72 (br. s, 1H); $^{13}$C NMR (100 MHz, CDCl$_3$) $\delta_C$/ppm 14.1, 15.1, 17.5, 20.8, 22.7, 26.2, 26.3, 29.4, 29.7, 31.2, 31.5, 31.8, 34.0, 35.2, 35.7, 35.9, 38.4, 39.1, 40.1, 43.4, 46.9, 49.6, 53.9, 95.0, 122.9, 170.8, 176.8, 199.4; HRMS (ESI) m/z calcd for $C_{28}H_{42}NaO_3$ [M+Na]$^+$: 449.3026 found: 449.3009; [α]$^{20}_{589}$=+34.6 (c 0.55, CHCl$_3$); IR ($v_{max}$/cm$^{-1}$): 1174, 1675, 1770, 2925.

Example 9

(+)-1α-(5-Bromopentyl)-4-androstene-3,17-dione (3)

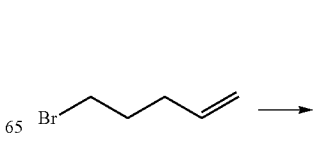

-continued

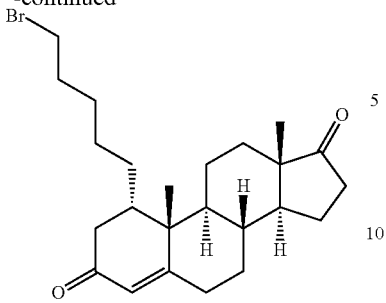

Procedure B: Cp₂ZrHCl (206 mg, 0.80 mmol, 2.0 eq.) was added to a stirred, room temperature, solution of 5-bromo-1-pentene (0.12 mL, 1.0 mmol, 2.5 eq.) in CH₂Cl₂ (0.40 mL) under an argon atmosphere. After stirring for about 15 min, the resulting clear yellow solution was transferred via syringe over about 1 min to a clear colourless stirred solution of CuOTf-ligand complex (30.0 mg, 0.040 mmol, 0.10 eq.) in Et₂O (2.0 mL) under an argon atmosphere. The resulting dark mixture was allowed to stir for an additional 10 min before 1,4-androstadiene-3,17-dione (114.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et₂O (ca 3 mL) and NH₄Cl (1 M aq., ca 1.5 mL). The mixture was partitioned between the aqueous and Et₂O layers and the former phase was extracted with Et₂O (3×10 mL). The combined organic phase was washed with NaHCO₃ (sat. aq., ca 10 mL), dried (Na₂SO₄), filtered and concentrated in vacuo to give an oil. Flash column chromatography of the yellow residue (10:30:60 EtOAc/DCM/petrol; SiO₂) gave major diastereomer (3) (+)-1α-(5-Bromopentyl)-4-androstene-3,17-dione (107 mg, 0.24 mmol, 60%) and minor diastereomer (3a) (+)-1α-(5-Bromopentyl)-4-androstene-3,17-dione (14 mg, 0.032 mmol, 8%). Diastereomeric ratio (4.8:1) was determined by integration of ¹H NMR spectra.

Major Diastereomer 3: ¹H NMR (400 MHz, CDCl₃) $\delta_H$/ppm 0.92 (s, 3H), 1.01-1.28 (m, 4H), 1.31 (s, 3H), 1.36-1.66 (m, 9H), 1.69-2.04 (m, 7H), 2.11 (dt, J=19.2, 9.0 Hz, 1H), 2.32-2.54 (m, 4H), 2.63 (dd, J=16.5, 4.4 Hz, 1H), 3.38 (t, J=6.7 Hz, 2H), 5.71 (br. s, 1H); ¹³C NMR (100 MHz, CDCl₃) $\delta_C$/ppm 13.7, 19.6, 20.5, 21.8, 26.6, 27.1, 28.4, 29.8, 31.2, 32.6, 32.7, 33.8, 35.0, 35.7, 37.9, 41.7, 41.8, 46.3, 47.5, 51.0, 124.0, 167.6, 198.8, 220.3; HRMS (ESI) m/z calcd for C₂₄H₃₅BrNaO₂ [M+Na]⁺: 457.1713 found: 457.1705; $[\alpha]^{20}_{589}$=+122.4 (c 1.055, CHCl₃); IR ($v_{max}$/cm⁻¹): 703, 1051, 1669, 1737, 2934.

Minor Diastereomer: HRMS (ESI) m/z calcd for C₂₄H₃₅BrNaO₂ [M+Na]⁺: 457.1713 found: 457.1710; $[\alpha]^{24}_{589}$=+5.4 (c 0.7, CHCl₃); IR ($v_{max}$/cm⁻¹): 1219, 1672, 1738, 2937.

Example 10

(+)-α-(5-Bromopentyl)-17α-hydroxy-3-oxo-pregn-4-ene-21-carboxylic acid γ-lactone (4)

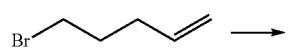

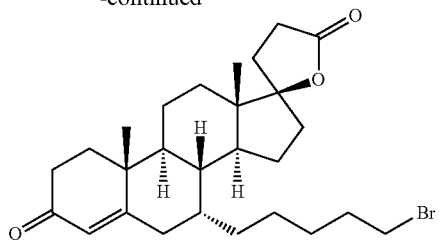

Procedure B: Cp₂ZrHCl (206 mg, 0.80 mmol, 2.0 eq.) was added to a stirred, room temperature, solution of 5-bromo-1-pentene (0.12 mL, 1.0 mmol, 2.5 eq.) in CH₂Cl₂ (0.40 mL) under an argon atmosphere. After stirring for about 15 min, the resulting clear yellow solution was transferred via syringe over about 1 min to a clear colourless stirred solution of CuOTf-ligand complex (30.0 mg, 0.040 mmol, 0.10 eq.) in Et₂O (2.0 mL) under an argon atmosphere. The resulting dark mixture was allowed to stir for an additional 10 min before Canrenone (136.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et₂O (ca 3 mL) and NH₄Cl (1 M aq., ca 1.5 mL). The mixture was partitioned between the aqueous and Et₂O layers and the former phase was extracted with Et₂O (3×10 mL). The combined organic phase was washed with NaHCO₃ (sat. aq., ca 10 mL), dried (Na₂SO₄), filtered and concentrated in vacuo to give an oil. Flash column chromatography of the yellow residue (30:70 EtOAc/petrol; SiO₂) gave major diastereomer (4) (+)-7α-(5-bromopentyl)-17α-hydroxy-3-oxo-pregn-4-ene-21-carboxylic acid γ-lactone (64 mg, 0.13 mmol, 33%) and minor diastereomer (4a) (+)-1α-(5-bromopentyl)-4-androstene-3,17-dione (14 mg, 0.028 mmol, 7%). Diastereomeric ratio was determined by integration of ¹H NMR spectra.

Major Diastereomer: ¹H NMR (400 MHz, CDCl₃) $\delta_H$/ppm 0.96-1.01 (m, 3H), 1.08-1.19 (m, 3H), 1.27-1.52 (m, 7H), 1.53-1.89 (m, 10H), 1.91-2.00 (m, 1H), 2.02-2.11 (m, 1H), 2.20-2.48 (m, 6H), 2.48-2.63 (m, 2H), 3.40 (t, J=6.7 Hz, 2H), 5.72 (br. s, 1H); ¹³C NMR (100 MHz, CDCl₃) $\delta_C$/ppm 14.4, 18.1, 20.7, 22.4, 25.1, 26.5, 28.4, 29.3, 31.2, 31.5, 32.7, 33.95, 33.99, 35.3, 36.0 (2C), 36.5, 38.6, 39.3, 44.8, 45.6, 46.9, 95.8, 125.9, 169.3, 176.7, 199.1; HRMS (ESI) m/z calcd for C₂₇H₃₉BrNaO₃ [M+Na]⁺: 513.1975 found: 513.1961; $[\alpha]^{20}_{589}$=+32.1 (c 0.80, CHCl₃); IR ($v_{max}$/cm⁻¹): 728, 913, 1663, 1767, 2939.

(+)-7α-(5-Bromopentyl)-17α-hydroxy-3-oxo-pregn-4-ene-21-carboxylic acid γ-lactone (4a): HRMS (ESI) m/z calcd for C₂₇H₃₉BrNaO₃ [M+Na]⁺: 513.1975 found: 513.1973; $[\alpha]^{24}_{589}$=+16.5 (c 0.49, CHCl₃); IR ($v_{max}$/cm⁻¹): 754, 1266, 1673, 1769, 2944.

Example 11

(+)-1α-(4-(chloromethyl)phenethyl)-4-androstene-3,17-dione (5)

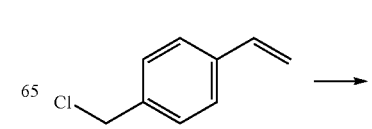

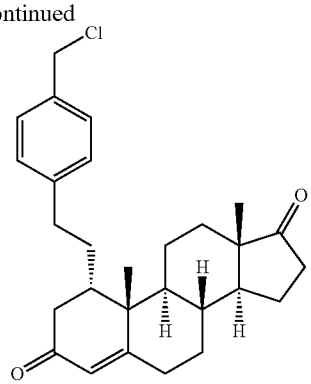

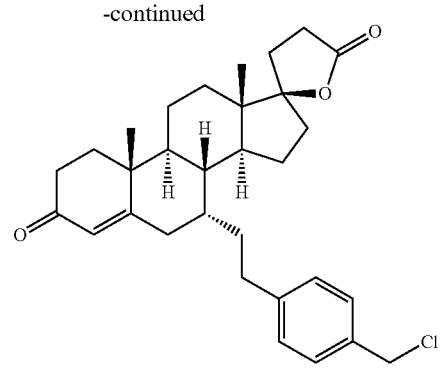

Procedure B: Cp$_2$ZrHCl (206 mg, 0.80 mmol, 2.0 eq.) was added to a stirred, room temperature, solution of 4-vinylbenzyl chloride (0.14 mL, 1.0 mmol, 2.5 eq.) in CH$_2$Cl$_2$ (0.40 mL) under an argon atmosphere. After stirring for about 15 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before 1,4-androstadiene-3,17-dione (114.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et$_2$O (ca 3 mL) and NH$_4$Cl (1 M aq., ca 1.5 mL). The mixture was partitioned between the aqueous and Et$_2$O layers and the former phase was extracted with Et$_2$O (3×10 mL). The combined organic phase was washed with NaHCO$_3$ (sat. aq., ca 10 mL), dried (Na$_2$SO$_4$), filtered and concentrated in vacuo to give an oil. Flash column chromatography of the yellow residue (5:35:60→10:30:60 EtOAc/DCM/petrol; SiO$_2$) gave major diastereomer (5) (+)-1α-(4-(chloromethyl)phenethyl))-4-androstene-3,17-dione (54 mg, 0.12 mmol, 30%), minor diastereomer (5a) (+)-1α-(4-(chloromethyl)phenethyl))-4-androstene-3,17-dione was not isolated.

Major Diastereomer: $^1$H NMR (400 MHz, CDCl$_3$) $\delta_H$/ppm 0.90 (s, 3H), 0.98-1.28 (m, 3H), 1.29 (s, 3H), 1.33-1.43 (m, 3H), 1.43-1.64 (m, 2H), 1.64-1.77 (m, 2H), 1.81 (dt, J=12.9, 3.1 Hz, 1H), 1.86-2.03 (m, 3H), 2.09 (dt, J=19.2, 9.0 Hz, 1H), 2.32-2.52 (m, 4H), 2.57 (dd, J=16.6, 1.6 Hz, 1H), 2.68 (dd, J=16.6, 3.3 Hz, 1H), 2.73-2.82 (m, 1H), 4.56 (br. s, 2H), 5.74 (br. s, 1H), 7.12 (d, J=8.2 Hz, 2H), 7.29 (d, J=8.2 Hz, 2H); $^{13}$C NMR (100 MHz, CDCl$_3$) $\delta_C$/ppm 13.7, 19.4, 20.4, 21.7, 29.4, 29.8, 31.1, 32.6, 33.2, 35.0, 35.7, 37.9, 41.1, 41.8, 46.1, 46.4, 47.5, 51.0, 124.0, 128.7 (2C), 128.8 (2C), 135.2, 142.2, 167.6, 198.5, 220.2; HRMS (ESI) m/z calcd for C$_{28}$H$_{35}$ClNaO$_2$ [M+Na]$^+$: 461.2218 found: 461.2204; $[\alpha]^{20}_{589}$=+125.0 (c 0.28, CHCl$_3$); IR ($v_{max}$/cm$^{-1}$): 730, 1667, 1737, 2934.

Procedure B: Cp$_2$ZrHCl (206 mg, 0.80 mmol, 2.0 eq.) was added to a stirred, room temperature, solution of 4-vinylbenzyl chloride (0.14 mL, 1.0 mmol, 2.5 eq.) in CH$_2$Cl$_2$ (0.40 mL) under an argon atmosphere. After stirring for about 15 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before Canrenone (136.0 mg, 0.40 mmol, 1.0 eq.) and TMSCl (0.26 mL, 2.00 mmol, 5.0 eq.) were added sequentially dropwise via syringe. Stirring at room temperature was continued arbitrarily for 15 h before the reaction was quenched by the addition of Et$_2$O (ca 3 mL) and NH$_4$Cl (1 M aq., ca 1.5 mL). The mixture was partitioned between the aqueous and Et$_2$O layers and the former phase was extracted with Et$_2$O (3×10 mL). The combined organic phase was washed with NaHCO$_3$ (sat. aq., ca 10 mL), dried (Na$_2$SO$_4$), filtered and concentrated in vacuo to give an oil. Flash column chromatography of the yellow residue (35:65 EtOAc/petrol; SiO$_2$) gave major diastereomer (6) (+)-7α-(4-(chloromethyl)phenethyl)-17α-hydroxy-3-oxo-pregn-4-ene-21-carboxylic acid γ-lactone (68 mg, 0.14 mmol, 35%), minor diastereomer (6a) (+)-7α-(4-(chloromethyl)phenethyl)-17α-hydroxy-3-oxo-pregn-4-ene-21-carboxylic acid γ-lactone was not isolated.

Major Diastereomer: $^1$H NMR (400 MHz, CDCl$_3$) $\delta_H$/ppm 0.97 (s, 3H), 1.10-1.21 (m, 1H), 1.24 (br. s., 3H), 1.27-1.85 (m, 13H), 1.86-1.94 (m, 1H), 2.01-2.12 (m, 1H), 2.16-2.27 (m, 1H), 2.28-2.60 (m, 8H), 2.69-2.79 (m, 1H), 4.56 (s, 2H), 5.82 (br. s, 1H), 7.13 (d, J=8.1 Hz, 2H), 7.30 (d, J=8.1 Hz, 2H); $^{13}$C NMR (100 MHz, CDCl$_3$) $\delta_C$/ppm 14.3, 18.2, 20.7, 22.2, 27.7, 29.2, 31.2, 31.4, 33.3, 34.0, 35.3, 35.7, 36.0, 36.4, 38.6, 39.3, 44.7, 45.6, 46.1, 47.0, 95.7, 126.0, 128.77 (2C), 128.81 (2C), 135.3, 142.5, 169.1, 176.7, 199.0; HRMS (ESI) m/z calcd for C$_{31}$H$_{39}$ClNaO$_3$ [M+Na]$^+$: 517.2480 found: 517.2463; $[\alpha]^{20}_{589}$=+64.0 (c 0.88, CHCl$_3$); IR ($v_{max}$/cm$^{-1}$): 727, 1663, 1765, 2945.

Example 13

(+)-7α-(4-(4,4,5,5-tetramethyl-1,3,2-dioxaborolan-2-yl)phenethyl)-17α-hydroxy-3-oxo-pregn-4-ene-21-carboxylic acid γ-lactone (7)

Example 12

(+)-7α-(4-(chloromethyl)phenethyl)-17α-hydroxy-3-oxo-pregn-4-ene-21-carboxylic acid γ-lactone (6)

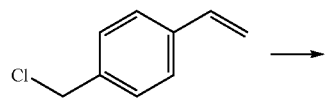

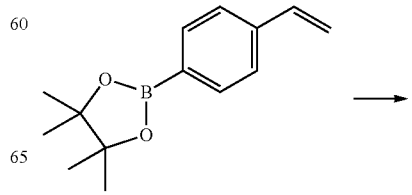

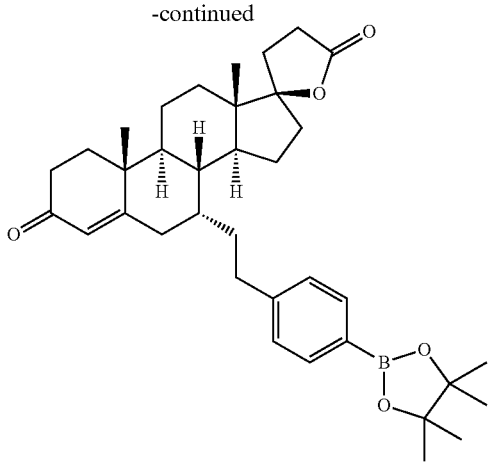

Procedure B: Cp$_2$ZrHCl (206 mg, 0.80 mmol, 2.0 eq.) was added to a stirred, room temperature, solution of (230.0 mg, 1.0 mmol, 2.5 eq.) in CH$_2$Cl$_2$ (0.40 mL) under an argon atmosphere. After stirring for about 15 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before Canrenone (136.0 mg, 0.40 mmol, 1.0 eq.) and TMSCl (0.26 mL, 2.0 mmol, 5.0 eq.) were added sequentially dropwise via syringe. Stirring at room temperature was continued arbitrarily for 15 h before the reaction was quenched by the addition of Et$_2$O (ca 3 mL) and NH$_4$Cl (1 M aq., ca 1.5 mL). The mixture was partitioned between the aqueous and Et$_2$O layers and the former phase was extracted with Et$_2$O (3×10 mL). The combined organic phase was washed with NaHCO$_3$ (sat. aq., ca 10 mL), dried (Na$_2$SO$_4$), filtered and concentrated in vacuo to give an oil. Flash column chromatography of the yellow residue (30:70 EtOAc/petrol; SiO$_2$) gave major diastereomer (7) (+)-7α-(4-(4,4,5,5-tetramethyl-1,3,2-dioxaborolan-2-yl) phenethyl)-17α-hydroxy-3-oxo-pregn-4-ene-21-carboxylic acid γ-lactone (104 mg, 0.18 mmol, 45%), minor diastereomer (7a) (+)-7α-(4-(4,4,5,5-tetramethyl-1,3,2-dioxaborolan-2-yl)phenethyl)-17α-hydroxy-3-oxo-pregn-4-ene-21-carboxylic acid γ-lactone was not isolated.

$^{13}$C NMR (100 MHz, CDCl$_3$) δ$_C$/ppm 14.3, 18.1, 20.7, 22.2, 24.8 (5C), 27.5, 29.3, 31.2, 31.4, 33.7, 34.0, 35.3, 35.6, 36.0, 36.4, 38.6, 39.2, 44.7, 45.6, 46.9, 83.7 (2C), 95.8, 126.0, 127.9 (2C), 135.0 (2C), 145.4, 169.2, 176.8, 199.1; HRMS (ESI) m/z calcd for C$_{36}$H$_{49}$BNaO$_5$ [M+Na]$^+$: 595.3565 found: 595.3562; [α]$^{24}_{589}$=+50.4 (c 0.51, CHCl$_3$); IR (v$_{max}$/cm$^{-1}$): 1360, 1666, 1769, 2976.

Example 14

(S)-4-(4-methoxyphenethyl)cyclohexanone

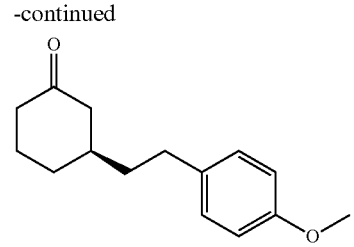

Procedure A: (CuOTf)$_2$.(C$_6$H$_6$) (10.1 mg, 0.02 mmol, 0.05 eq.) and the phosphoramidite ligand (21.6 mg, 0.040 mmol, 0.10 eq.) were dissolved in Et$_2$O (2.0 mL) under an argon atmosphere and allowed to stir for 1 h at room temperature. In another flask, Cp$_2$ZrHCl (206.0 mg, 0.80 mmol, 2.0 eq.) was added to a stirred, room temperature, solution of 4-methoxystyrene (0.13 mL, 1.0 mmol, 2.5 eq.) in CH$_2$Cl$_2$ (0.40 mL) under an argon atmosphere. After stirring for 15 min, the resulting clear red/orange solution was transferred via syringe over about 1 min to the stirred solution containing the copper and ligand under an argon atmosphere. The resulting black mixture was allowed to stir for an additional 10 minutes before cyclohexenone (39 μL, 0.40 mmol, 1.0 eq) and then TMSCl (0.26 mL, 2.0 mmol, 5.0 eq.) were added dropwise via syringe. Stirring continued at room temperature for 4 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo. Flash column chromatography of the yellow residue (1:9 EtOAc/petrol; SiO$_2$) gave (R)-3-(4-methoxyphenethyl)cyclohexanone (45 mg, 0.19 mmol, 48%) as a colourless oil. HPLC analysis indicated an enantiomeric excess of 90% [Chiralpak® IA; flow: 1 mL/min; hexane/i-PrOH: 90:10; λ=210 nm; minor enantiomer (S)-3-(4-methoxyphenethyl)-cyclohexanone, t$_R$=11.4 minutes; major enantiomer (R)-3-(4-methoxyphenethyl)-cyclohexanone, t$_R$=12.2 minutes]. $^1$H NMR (500 MHz, CDCl$_3$) δ$_H$/ppm 1.33-1.44 (m, 1H) 1.55-1.71 (m, 3H) 1.81 (apparent tspt, J=11.03, 3.50 Hz, 1H) 1.92-1.99 (m, 1H) 2.02-2.10 (m, 2H) 2.27 (dddd, J=13.70, 12.50, 6.50, 1.40 Hz, 1H) 2.33-2.40 (m, 1H) 2.48 (ddt, J=13.75, 4.14, 1.93, 1.93 Hz, 1H) 2.58 (t, J=8.04 Hz, 2H) 3.79 (s, 3H) 6.83 (d, J=8.83 Hz, 2H) 7.09 (d, J=8.80 Hz, 2H); $^{13}$C NMR (126 MHz, CDCl$_3$) δ$_C$/ppm 25.2, 31.2, 32.0, 38.4, 38.6, 41.5, 48.0, 55.2, 113.8 (2C), 129.1 (2C), 134.0, 157.8, 211.8; HRMS (ESI) m/z calcd for C$_{16}$H$_{20}$NaO$_2$ [M+Na]$^+$: 255.1356 found: 255.1349; [α]$^{24}_{589}$=−20.1 (c 1.03, CHCl$_3$); IR (v$_{max}$/cm$^{-1}$): 1710, 2933.

Example 15

(R)-4-(4-methoxyphenethyl)cyclohexanone

-continued

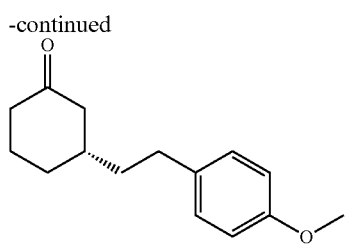

Procedure A: (CuOTf)$_2$·(C$_6$H$_6$) (10.1 mg, 0.02 mmol, 0.05 eq.) and the phosphoramidite ligand (21.6 mg, 0.040 mmol, 0.10 eq.) were dissolved in Et$_2$O (2.0 mL) under an argon atmosphere and allowed to stir for 1 h at room temperature. In another flask, Cp$_2$ZrHCl (206.0 mg, 0.80 mmol, 2.0 eq.) was added to a stirred, room temperature, solution of 4-methoxystyrene (0.13 mL, 1.0 mmol, 2.5 eq.) in CH$_2$Cl$_2$ (0.40 mL) under an argon atmosphere. After stirring for 15 min, the resulting clear red/orange solution was transferred via syringe over about 1 min to the stirred solution containing the copper and ligand under an argon atmosphere. The resulting black mixture was allowed to stir for an additional 10 minutes before cyclohexenone (39 μL, 0.40 mmol, 1.0 eq) and then TMSCl (0.26 mL, 2.0 mmol, 5.0 eq.) were added dropwise via syringe. Stirring continued at room temperature for 4 h before the reaction was quenched by the addition of Et$_2$O (ca 3 mL) and then NH$_4$Cl (1M aq., ca 1.5 mL). The mixture was partitioned between the aqueous and Et$_2$O layers and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo.

Example 16

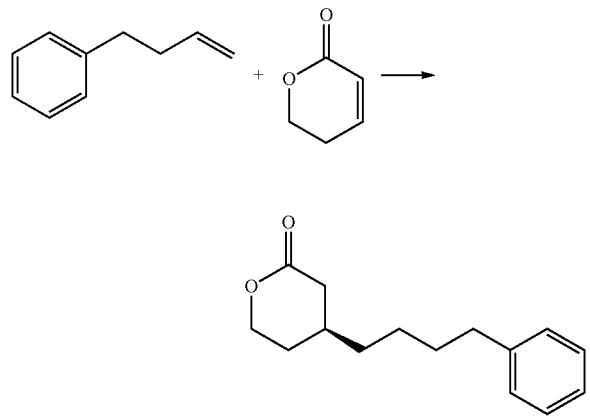

Cp$_2$ZrHCl (206 mg, 0.80 mmol, 2.0 eq.) was added to a stirred, room temperature, solution of 4-phenyl-1-butene (0.15 mL, 1.0 mmol, 2.5 eq.) in CH$_2$Cl$_2$ (0.40 mL) under an argon atmosphere. After stirring for about 20 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before 5,6-dihydropyran-2-one (0.034 mL, 0.40 mmol, 1.0 eq.) and then TMSCl (0.25 mL, 2.0 mmol, 5.0 eq.) were added dropwise via syringe. The reaction was stirred until complete (TLC control (EtOAc/Petrol 3:7)). The reaction was quenched by the addition of Et$_2$O (ca 3 mL) and then NH$_4$Cl (1 M. aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo to give an oil. Flash column chromatography of the residue (EtOAc/petrol; SiO$_2$) gave (−)-(S)-4-(4-phenylbutyl)-5,6-dihydropyran-2-one (32.5 mg, 0.14 mmol, 36%) as a colourless oil. HPLC analysis indicated an enantiomeric excess of 79% [Chiralpak® IA; flow 1 ml/min; hexane/i-PrOH: 99:1; λ=210 nm; minor enantiomer (+)-(R)-4-(4-phenylbutyl)-5,6-dihydropyran-2-one, $t_R$=40.97 min; major enantiomer (−)-(S)-4-(4-phenylbutyl)-5,6-dihydropyran-2-one, $t_R$=45.98 min].

Example 17

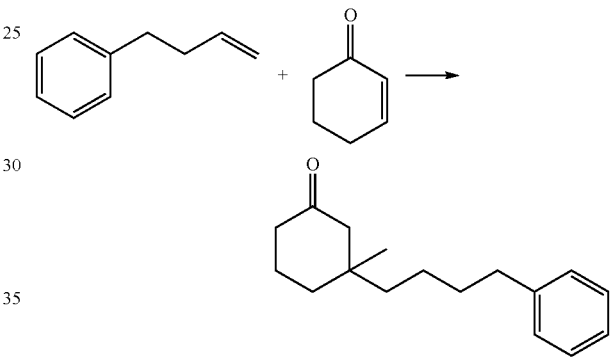

Cp$_2$ZrHCl (103 mg, 0.40 mmol, 2.0 eq.) was added to a stirred, room temperature, solution of 4-phenyl-1-butene (0.08 mL, 0.5 mmol, 2.5 eq.) in CH$_2$Cl$_2$ (0.40 mL) under an argon atmosphere. After stirring for about 20 min, the resulting clear yellow solution was transferred via syringe over about 1 min to a clear colourless stirred solution of CuOTf-ligand complex (15.0 mg, 0.020 mmol, 0.10 eq.) in Et$_2$O (2.0 mL) under an argon atmosphere. The resulting dark mixture was allowed to stir for an additional 10 min before 3-methyl-2-cyclohexenone (0.023 mL, 0.20 mmol, 1.0 eq.) and then TMSCl (0.13 mL, 1.0 mmol, 5.0 eq.) were added dropwise via syringe. The reaction was stirred until complete (TLC control (EtOAc/Petrol 1:9)). The reaction was quenched by the addition of Et$_2$O (ca 3 mL) and then NH$_4$Cl (1 M. aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo to give an oil. Flash column chromatography of the residue (EtOAc/petrol; SiO$_2$) gave (−)-3-methyl-3-(4-phenylbutyl)cyclohexenone (21.9 mg, 0.09 mmol, 45%) as a yellow oil. HPLC analysis indicated an enantiomeric excess of 60% [Chiralpak® IA; flow 1 ml/min; hexane/i-PrOH: 99:1; λ=210 nm; minor enantiomer (+)-3-methyl-3-(4-phenylbutyl)cyclohexenone, $t_R$=14.90 min; major enantiomer (−)-3-methyl-3-(4-phenylbutyl)cyclohexenone, $t_R$=15.70 min].

Example 18

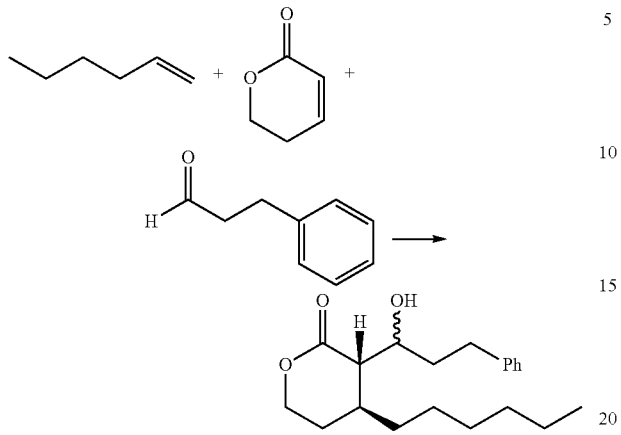

Cp$_2$ZrHCl (206 mg, 0.80 mmol, 2.0 eq.) was added to a stirred, room temperature, solution of 1-hexene (0.12 mL, 1.0 mmol, 2.5 eq.) in CH$_2$Cl$_2$ (0.40 mL) under an argon atmosphere. After stirring for about 30 min, the resulting clear yellow solution was transferred via syringe over about 1 min to a clear colourless stirred solution of CuOTf-ligand complex (30.0 mg, 0.040 mmol, 0.10 eq.) in Et$_2$O (2.0 mL) under an argon atmosphere. The resulting dark mixture was allowed to stir for an additional 10 min before 5,6-dihydropyran-2-one (0.034 mL, 0.40 mmol, 1.0 eq.), 3-phenylpropionaldehyde and then TMSCl (0.25 mL, 2.0 mmol, 5.0 eq.) were added dropwise via syringe. The reaction was stirred until complete (TLC control (EtOAc/Petrol 3:7)). The reaction was quenched by the addition of Et$_2$O (ca 3 mL) and then NH$_4$Cl (1 M. aq., ca 1.5 mL). The mixture was partitioned between water and Et$_2$O and the aqueous phase extracted with Et$_2$O (3×10 mL). The combined organic phase was washed with NaHCO$_3$ (aq. sat., ca 10 mL), dried (Na$_2$SO$_4$), filtered and concentrated in vacuo to give an oil. Flash column chromatography of the residue (17:83 EtOAc/petrol; SiO$_2$) gave (+)-(S,S,S)-3-(3-phenylpropan-1-ol)-4-hexyl-5,6-dihydropyran-2-one (71.3 mg, 0.022 mmol, 56%) as an oil. HPLC analysis indicated a diastereomeric ratio of 2:1 and an enantiomeric excess of 81%:77% (major: minor) [Chiralpak® IA; flow 1.5 ml/min; hexane/i-PrOH: 98:2; λ=210 nm; diastereomer1: minor enantiomer (R,R,R)-3-(3-phenylpropan-1-ol)-4-hexyl-5,6-dihydropyran-2-one, $t_R$=16.65 min; major enantiomer (S,S,S)-3-(3-phenylpropan-1-ol)-4-hexyl-5,6-dihydropyran-2-one, $t_R$=18.65 min; diastereomer 2: minor enantiomer (R,R,S)-3-(3-phenylpropan-1-ol)-4-hexyl-5,6-dihydropyran-2-one, $t_R$=24.53 min; major enantiomer (S,S,R)-3-(3-phenylpropan-1-ol)-4-hexyl-5,6-dihydropyran-2-one, $t_R$=25.53 min].

It will be understood that the present invention has been described above purely by way of example, and modification of detail can be made within the scope of the invention. Each feature disclosed in the description, and where appropriate the claims and drawings may be provided independently or in any appropriate combination.

The invention claimed is:
1. A process for producing a chiral compound in a stereoisomeric excess, the process comprising:
(i) contacting a first compound comprising an alkene bond with a hydrometallating agent, wherein the first compound and the hydrometallating agent are contacted under conditions such that the first compound is hydrometallated by said hydrometallating agent; and
(ii) contacting the hydrometallated first compound with a second compound, wherein the second compound comprises a conjugated π-bond system which is capable of undergoing a 1,4-conjugate addition reaction and which has a carbon atom at said 4-position, wherein the hydrometallated first compound and the second compound are contacted under conditions such that they undergo an asymmetric 1,4-conjugate addition reaction in which a carbon atom of said hydrometallated first compound binds to the carbon atom at said 4-position of the second compound, forming a stereoisomeric excess of a compound having a chiral carbon atom at said 4-position, wherein said asymmetric conjugate addition reaction is performed in the presence of a metal catalyst comprising a non-racemic chiral ligand;
wherein:
the hydrometallating agent is HZrCp$_2$Cl;
the second compound is an α,β-unsaturated carbonyl compound;
the metal catalyst comprises copper (I); and
the non-racemic chiral ligand is a phosphoramidite ligand.
2. A process for producing a chiral compound of the formula (IV) in a stereoisomeric excess:

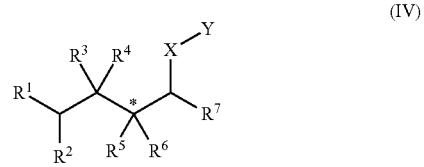

(IV)

wherein
R$^1$, R$^2$, R$^3$ and R$^4$ are each independently selected from hydrogen, R$^a$, hydrocarbyl optionally substituted with 1, 2, 3, 4 or 5 R$^a$; and —(CH$_2$)$_j$-heterocyclyl optionally substituted with 1, 2, 3, 4 or 5 R$^a$;
or R$^1$ and R$^3$ taken together with the carbon atoms to which they are attached may form a carbocyclic or heterocyclic group, which group is optionally substituted with 1, 2, 3, 4 or 5 R$^a$;
R$^5$, R$^6$ and R$^7$ are each independently selected from hydrogen, R$^a$, hydrocarbyl optionally substituted with 1, 2, 3, 4 or 5 R$^a$; and —(CH$_2$)$_j$-heterocyclyl optionally substituted with 1, 2, 3, 4 or 5 R$^a$;
or R$^5$ and one of R$^7$ and X, taken together with the carbon atoms to which they are attached, may form a carbocyclic or heterocyclic group, which group is optionally substituted with 1, 2, 3, 4 or 5 R$^a$;
X and Y taken together form —C(O)R$^8$, —C(O)OR$^8$, —C(O)NR$^8$R$^9$, —C(O)SR$^8$ or —C(O)SeR$^8$, wherein R$^8$ and R$^9$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy; or
X is carbon and Y is oxo; and X and R$^5$ taken together with the carbon atoms to which they are attached form a carbocyclic group or a heterocyclic group, either of which is optionally substituted with 1, 2, 3, 4 or 5 R$^a$;
each R$^a$ is independently selected from halogen, trifluoromethyl, cyano, nitro, oxo, =NR$^b$, —OR$^b$, —C(O)R$^b$, —C(O)N(R$^b$)R$^c$, —C(O)OR$^b$, —C(O)SR$^b$, —C(O)

SeR$^b$, —OC(O)R$^b$, —S(O)$_k$R$^b$, —S(O)$_k$N(R$^b$)R$^c$, —N(R$^b$)R$^c$, —N(R$^b$)N(R$^b$)R$^c$, —N(R$^b$)C(O)R$^c$ and —N(R$^b$)S(O)$_k$R$^b$;

R$^b$ and R$^c$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy;

j is 0, 1, 2, 3, 4, 5 or 6;

k is 0, 1 or 2; and the asterisk * designates a chiral center of (R) or (S) configuration;

wherein the process comprises:

(i) contacting a compound comprising an alkene bond with a hydrometallating agent of the formula HZrCp$_2$Cl, wherein M comprises a metal, wherein said compound and the hydrometallating agent are contacted under conditions such that they react to form a compound of the formula (II):

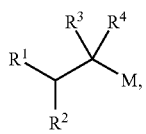

(II)

wherein M is ZrCp$_2$Cl; and (ii) contacting the compound of the formula (II) with a compound of the formula (III):

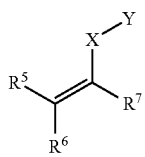

(III)

wherein the compound of formula (II) and the compound of formula (III) are contacted under conditions such that they undergo an asymmetric 1,4-conjugate addition reaction to form a stereoisomeric excess of a compound of formula (IV), wherein said asymmetric conjugate addition reaction is performed in the presence of a metal catalyst comprising a non-racemic chiral ligand, wherein the metal catalyst comprises copper (I) and the non-racemic chiral ligand is a phosphoramidite ligand.

3. A process according to claim 2, wherein said compound comprising an alkene bond is a compound of the formula (I):

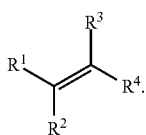

(I)

4. A process according to claim 2, wherein R$^1$ is hydrocarbyl optionally substituted with 1, 2, 3, 4 or 5 R$^a$.

5. A process according to claim 2, wherein R$^3$ is hydrogen or hydrocarbyl optionally substituted with 1, 2, 3, 4 or 5 R$^a$.

6. A process according to claim 2, wherein R$^1$ and R$^3$ taken together with the carbon atoms to which they are attached form, in the compounds of formulae (II) and (IV), cycloalkyl optionally substituted with 1, 2, 3, 4 or 5 R$^a$.

7. A process according to claim 2, wherein R$^2$ and R$^4$ are each hydrogen.

8. A process according to claim 2, wherein the chiral compound is produced in an enantiomeric excess or a diastereomeric excess.

9. A process according to claim 2, wherein the process further comprises formulating a product comprising the chiral compound or converting the chiral compound into a product.

10. A process for producing a chiral compound in a stereoisomeric excess, the process comprising:

(i) contacting a first compound comprising an alkene bond with a hydrometallating agent, wherein the first compound and the hydrometallating agent are contacted under conditions such that the first compound is hydrometallated by said hydrometallating agent; and (ii) contacting the hydrometallated first compound with a second compound, wherein the second compound comprises a conjugated π-bond system which is capable of undergoing a 1,6-conjugate addition reaction and which has a carbon atom at said 6-position, wherein the hydrometallated first compound and the second compound are contacted under conditions such that they undergo an asymmetric 1,6-conjugate addition reaction in which a carbon atom of said hydrometallated first compound binds to the carbon atom at said 6-position of the second compound, forming a stereoisomeric excess of a compound having a chiral carbon atom at said 6-position, wherein said asymmetric conjugate addition reaction is performed in the presence of a metal catalyst, said metal catalyst optionally comprising a non-racemic chiral ligand;

wherein:

the hydrometallating agent is HZrCp$_2$Cl;

the second compound is an unsaturated carbonyl compound comprising at least two alkene bonds that are conjugated with a carbonyl group;

the metal catalyst comprises copper (I); and the non-racemic chiral ligand is a phosphoramidite ligand.

11. A process for producing a chiral compound of the formula (VI) in a stereoisomeric excess:

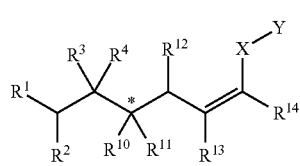

(VI)

wherein

R$^1$, R$^2$, R$^3$ and R$^4$ are each independently selected from hydrogen, R$^a$, hydrocarbyl optionally substituted with 1, 2, 3, 4 or 5 R$^a$; and —(CH$_2$)$_j$-heterocyclyl optionally substituted with 1, 2, 3, 4 or 5 R$^a$;

or R$^1$ and R$^3$ taken together with the carbon atoms to which they are attached may form a carbocyclic or heterocyclic group, which group is optionally substituted with 1, 2, 3, 4 or 5 R$^a$;

R$^{10}$, R$^{11}$, R$^{12}$, R$^{13}$ and R$^{14}$ are each independently selected from hydrogen, R$^a$, hydrocarbyl optionally substituted with 1, 2, 3, 4 or 5 R$^a$; and —(CH$_2$)$_j$-heterocyclyl optionally substituted with 1, 2, 3, 4 or 5 R$^a$;

or two or more of $R^{10}$, $R^{11}$, $R^{12}$, $R^{13}$, $R^{14}$ and X taken together with the carbon atoms to which they are attached, may form a carbocyclic or heterocyclic group, which group is optionally substituted with 1, 2, 3, 4 or 5 $R^a$;

X and Y taken together form —C(O)$R^8$, —C(O)O$R^8$, —C(O)N$R^8R^9$, —C(O)S$R^8$ or —C(O)Se$R^8$, wherein $R^8$ and $R^9$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy; or X is carbon and Y is oxo; and X and one or more of $R^{10}$, $R^{11}$, $R^{12}$, $R^{13}$ and $R^{14}$ taken together with the carbon atoms to which they are attached form a carbocyclic group or a heterocyclic group, either of which is optionally substituted with 1, 2, 3, 4 or 5 $R^a$;

each $R^a$ is independently selected from halogen, trifluoromethyl, cyano, nitro, oxo, =N$R^b$, —O$R^b$, —C(O)$R^b$, —C(O)N($R^b$)$R^c$, —C(O)O$R^b$, —C(O)S$R^b$, —C(O)Se$R^b$, —OC(O)$R^b$, —S(O)$_k$$R^b$, —S(O)$_k$N($R^b$)$R^c$, —N($R^b$)$R^c$, —N($R^b$)N($R^b$)$R^c$, —N($R^b$)C(O)$R^c$ and —N($R^b$)S(O)$_k$$R^b$;

$R^b$ and $R^c$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy;

j is 0, 1, 2, 3, 4, 5 or 6;
k is 0, 1 or 2; and
the asterisk * designates a chiral center of (R) or (S) configuration;

wherein the process comprises:
(i) contacting a compound comprising an alkene bond with a hydrometallating agent of the formula HZrCp$_2$Cl, wherein M comprises a metal, wherein said compound and the hydrometallating agent are contacted under conditions such that they react to form a compound of the formula (II):

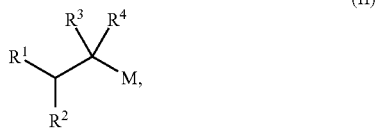

(II)

wherein M is ZrCp$_2$Cl; and
(ii) contacting the compound of the formula (II) with a compound of the formula (V):

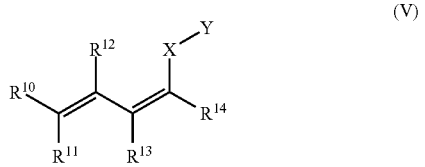

(V)

wherein the compound of formula (II) and the compound of formula (V) are contacted under conditions such that they undergo an asymmetric 1,6-conjugate addition reaction to form a stereoisomeric excess of a compound of formula (VI), wherein said asymmetric conjugate addition reaction is performed in the presence of a metal catalyst, said metal catalyst optionally comprising a non-racemic chiral ligand, wherein the metal catalyst comprises copper (I) and the non-racemic chiral ligand is a phosphoramidite ligand.

12. A process for producing a chiral compound of the formula (IVa) in a stereoisomeric excess:

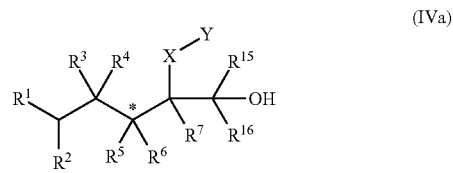

(IVa)

wherein
$R^1$, $R^2$, $R^3$ and $R^4$ are each independently selected from hydrogen, $R^a$, hydrocarbyl optionally substituted with 1, 2, 3, 4 or 5 $R^a$; and —(CH$_2$)$_j$-heterocyclyl optionally substituted with 1, 2, 3, 4 or 5 $R^a$;

or $R^1$ and $R^3$ taken together with the carbon atoms to which they are attached may form a carbocyclic or heterocyclic group, which group is optionally substituted with 1, 2, 3, 4 or 5 $R^a$;

$R^5$, $R^6$ and $R^7$ are each independently selected from hydrogen, $R^a$, hydrocarbyl optionally substituted with 1, 2, 3, 4 or 5 $R^a$; and —(CH$_2$)$_j$-heterocyclyl optionally substituted with 1, 2, 3, 4 or 5 $R^a$;

or $R^5$ and one of $R^7$ and X, taken together with the carbon atoms to which they are attached, may form a carbocyclic or heterocyclic group, which group is optionally substituted with 1, 2, 3, 4 or 5 $R^a$;

$R^{15}$ and $R^{16}$ are each independently selected from hydrogen, $R^a$, hydrocarbyl optionally substituted with 1, 2, 3, 4 or 5 $R^a$; and —(CH$_2$)$_j$-heterocyclyl optionally substituted with 1, 2, 3, 4 or 5 $R^a$;

X and Y taken together form —C(O)$R^8$, —C(O)O$R^8$, —C(O)N$R^8R^9$, —C(O)S$R^8$ or —C(O)Se$R^8$, wherein $R^8$ and $R^9$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy; or X is carbon and Y is oxo; and X and $R^5$ taken together with the carbon atoms to which they are attached form a carbocyclic group or a heterocyclic group, either of which is optionally substituted with 1, 2, 3, 4 or 5 $R^a$;

each $R^a$ is independently selected from halogen, trifluoromethyl, cyano, nitro, oxo, =N$R^b$, —O$R^b$, —C(O)$R^b$, —C(O)N($R^b$)$R^c$, —C(O)O$R^b$, —C(O)S$R^b$, —C(O)Se$R^b$, —OC(O)$R^b$, —S(O)$_k$$R^b$, —S(O)$_k$N($R^b$)$R^c$, —N($R^b$)$R^c$, —N($R^b$)N($R^b$)$R^c$, —N($R^b$)C(O)$R^c$ and —N($R^b$)S(O)$_k$$R^b$;

$R^b$ and $R^c$ are each independently hydrogen or selected from hydrocarbyl and —(CH$_2$)$_j$-heterocyclyl, either of which is optionally substituted with 1, 2, 3, 4 or 5 substituents independently selected from halogen, oxo, cyano, amino, hydroxy, alkyl and alkoxy;

j is 0, 1, 2, 3, 4, 5 or 6;
k is 0, 1 or 2; and
the asterisk * designates a chiral center of (R) or (S) configuration;

wherein the process comprises:
(i) contacting a compound comprising an alkene bond with a hydrometallating agent of the formula HZrCp$_2$Cl, wherein M comprises a metal, wherein said compound and the hydrometallating agent are contacted under conditions such that they react to form a compound of the formula (II):

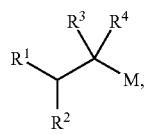
(II)

wherein M is ZrCp$_2$Cl; and (ii) contacting the compound of the formula (II) with a compound of the formula (III):

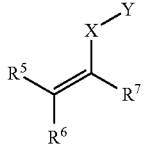
(III)

and a compound of the formula (VII):

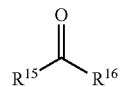
(VII)

wherein the compound of formula (II), the compound of formula (III) and the compound of formula (VII) are contacted under conditions such that they undergo an asymmetric 1,4-conjugate addition reaction to form a stereoisomeric excess of a compound of formula (IVa), wherein said asymmetric conjugate addition reaction is performed in the presence of a metal catalyst comprising a non-racemic chiral ligand, wherein the metal catalyst comprises copper (I) and the non-racemic chiral ligand is a phosphoramidite ligand.

* * * * *